(12) United States Patent
Edlund et al.

(10) Patent No.: US 11,691,954 B2
(45) Date of Patent: Jul. 4, 2023

(54) FORMULATIONS

(71) Applicant: BETAGENON AB, Umeå (SE)

(72) Inventors: Thomas Edlund, Umeå (SE); Jacob Westman, Järläsa (SE)

(73) Assignee: BETAGENON AB, Umeå (SE)

( * ) Notice: Subject to any disclaimer, the term of this patent is extended or adjusted under 35 U.S.C. 154(b) by 0 days.

(21) Appl. No.: 17/738,873

(22) Filed: May 6, 2022

(65) Prior Publication Data

US 2022/0267287 A1  Aug. 25, 2022

Related U.S. Application Data

(63) Continuation of application No. 17/769,666, filed as application No. PCT/GB2020/052618 on Oct. 16, 2020.

(30) Foreign Application Priority Data

Oct. 18, 2019 (GB) ..................................... 1915094

(51) Int. Cl.
 *C07D 285/08* (2006.01)
 *A61K 9/14* (2006.01)

(52) U.S. Cl.
 CPC .............. *C07D 285/08* (2013.01); *A61K 9/14* (2013.01)

(58) Field of Classification Search
 CPC ................................. C07D 285/08; A61K 9/14
 See application file for complete search history.

(56) References Cited

U.S. PATENT DOCUMENTS

| 9,162,994 | B2 * | 10/2015 | Westman | ............. | C07D 417/10 |
| 9,675,596 | B2 * | 6/2017 | Westman | ............. | A61K 31/433 |
| 2022/0023269 | A1 | 1/2022 | Edlund et al. | | |

FOREIGN PATENT DOCUMENTS

| EP | 2 451 794 B1 | 5/2012 |
| EP | 2451794 B1 | 5/2012 |
| WO | WO-2011004162 A2 | 1/2011 |
| WO | WO 2020/095010 A1 | 5/2020 |
| WO | WO-2020095010 A1 | 5/2020 |
| WO | WO-2021074646 A1 | 4/2021 |

OTHER PUBLICATIONS

International Search Report for PCT/USGB2020/052618 (dated Feb. 2, 2021).
Stenberg P. et al.: "PAN-AMPK activator 0304 improves glucose homeostasis and microvascular perfusion in mice and type 2 diabetes patients", JCI ISIGHT, vol. 3, No. 12, Jun. 21, 2018 (Jun. 21, 2018).
Cokorinos E.C, et al., Activation of Skeletal Muscle AMPK Promotes Glucose Disposal and Glucose Lowering in Non-human Primates and Mice. Cell Metab. 25(5):1147-1159, 2017.
Das V, et al., AMP-activated protein kinase (AMPK) activator drugs reduce mechanical allodynia in a mouse model of low back pain. Reg Anesth Pain Med 2019;0:1-5. doi:10.1136/rapm-2019-100839.
Das V, et al., Antihyperalgesia effect of AMP-activated protein kinase (AMPK) activators in a mouse model of postoperative pain. Reg Anesth Pain Med 2019;0:1-6. doi:10.1136/rapm-2019-100651.
Hardie D.G, AMPK-activated protein kinase—an energy sensor that regulates all aspects of cell function. Genes & Dev. 25, 1895-1908, 2011. http://www.genesdev.org/cgi/doi/10.1101/gad.17420111.
Hardie D.G, et. al., AMP-activated protein kinase: A Target for Drugs both Ancient and Modern. Chemistry Biol. 19(10): 1222-1236, 2012. doi:10.1016/j.chembiol.2012.08.019.
Loh et al., Overview of milling techniques for improving the solubility of poorly water-soluble drugs. Asian Journal of Pharmaceutical Sciences, 10 (2015), 255-274.
Myers R. W, et al., Systemic pan-AMPK activator MK-8722 improves glucose homeostasis but induces cardiac hypertrophy. Science 357, 507-511, 2017.
U.S. Dept. of Health and Human Services, National Cancer Institute. Common terminology criteria for adverse events, CTCAE v5.0, Nov. 27, 2017.
Nekkanti et al., Drug Nanoparticles—An Overview, The Delivery of Nanoparticles, ISBN: 978-953-51-0615-9, InTech, Available from: http://www.intechopen.com/books/the-delivery-of-nanoparticles/drug-nanoparticles-an-overview (2012).
Peltonen et al., Handbook of Polymers for Pharmaceutical Technologies, Polymeric Stabilizers for Drug Nanocrystals. ed. Thakur and Thakur, Wiley, vol. 4, chapter 3, 67-87 (2016).
Schulz E, et al., When Metabolism Rules Perfusion, AMPK-Mediated Endothelial Nitric Oxide Synthase Activation. Circulation Research. 104, 422-424, 2009.

\* cited by examiner

*Primary Examiner* — Kamal A Saeed
(74) *Attorney, Agent, or Firm* — Morrison & Foerster LLP

(57) ABSTRACT

There is provided an alkali metal salt of 4-chloro-N-[2-[(4-chlorophenyl)methyl]-3-oxo-1,2,4-thiadiazol-5-yl]benz-amide and formulations thereof. This salt finds particular utility in the treatment or prevention of a disorder or condition ameliorated by the activation of AMPK.

47 Claims, 5 Drawing Sheets

FORMULATIONS

CROSS-REFERENCE TO RELATED APPLICATIONS

This application is a continuation, and claims the benefit under 35 U.S.C. § 120, of U.S. patent application Ser. No. 17/769,666, filed Apr. 15, 2022, which claims the benefit under 35 U.S.C. § 119, of PCT patent application no. PCT/GB2020/052618, filed Oct. 16, 2020, which claims the benefit under 35 U.S.C. § 119, of United Kingdom patent application serial no. 1915094.5, filed Oct. 18, 2019, the entire disclosures of which are hereby incorporated by reference.

FIELD OF THE INVENTION

The present invention relates to alkali metal salts of a particular pharmaceutical active ingredient, and the use of such salts in medicine, in particular, the present invention relates to oral formulations comprising milled alkali metal salts of the active ingredient.

BACKGROUND OF THE INVENTION

AMP-activated protein kinase (AMPK) is a protein kinase enzyme that consists of three protein sub-units and is activated by hormones, cytokines, exercise, and stresses that diminish cellular energy state (e.g. glucose deprivation). Activation of AMPK increases processes that generate adenosine 5'-triphosphate (ATP) (e.g., fatty-acid oxidation) and restrains others such as fatty acid-, glycerolipid- and protein-synthesis that consume ATP, but are not acutely necessary for survival. Conversely, when cells are presented with a sustained excess of glucose, AMPK activity diminishes and fatty acid-, glycerolipid- and protein-synthesis are enhanced. AMPK thus is a protein kinase enzyme that plays an important role in cellular energy homeostasis. Therefore, the activation of AMPK is coupled to glucose lowering effects and triggers several other biological effects, including the inhibition of cholesterol synthesis, lipogenesis, triglyceride synthesis, and the reduction of hyperinsulinemia.

Given the above, AMPK is a preferred target for the treatment of the metabolic syndrome and especially type 2 diabetes. AMPK is also involved in a number of pathways that are important for many different diseases (e.g. AMPK is also involved in a number of pathways that are important in CNS disorders, fibrosis, osteoporosis, heart failure and sexual dysfunction).

AMPK is also involved in a number of pathways that are important in cancer. Several tumour suppressors are part of the AMPK pathway AMPK acts as a negative regulator of the mammalian TOR (mTOR) and EF2 pathway, which are key regulators of cell growth and proliferation. The deregulation may therefore be linked to diseases such as cancer (as well as diabetes). AMPK activators may therefore be of utility as anti-cancer drugs.

4-Chloro-N-[2-[(4-chlorophenyl)methyl]-3-oxo-1,2,4-thiadiazol-5-yl]benzamide (i.e. the compound of formula I) was first disclosed in WO 2011/004162 and has been shown to be an AMPK activator.

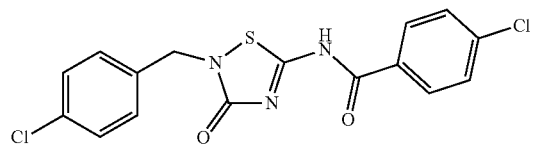

As an AMPK agonist (i.e. an AMPK activator), the compound of formula I is useful in the treatment of disorders or conditions which are ameliorated by the activation of AMPK. Such compounds may be useful in the treatment of cancer, diabetes, cardiovascular diseases, hyperinsulinemia and associated conditions, a condition/disorder where fibrosis plays a role, sexual dysfunction, osteoporosis and neurodegenerative diseases.

There remains a need to improve the bioavailability of active ingredients, such as 4-chloro-N-[2-[(4-chlorophenyl)methyl]-3-oxo-1,2,4-thiadiazol-5-yl]benzamide, in vivo so as to improve their effectiveness in medicine. The inventors have now found that the use of particular salts of the compound of formula I surprisingly enhances the bioavailability for said compound in vivo.

The listing or discussion of an apparently prior-published document in this specification should not necessarily be taken as an acknowledgement that the document is part of the state of the art or is common general knowledge.

DETAILED DESCRIPTION OF THE INVENTION

According to a first aspect of the invention, there is provided an alkali metal salt of 4-chloro-N-[2-[(4-chlorophenyl)methyl]-3-oxo-1,2,4-thiadiazol-5-yl]benzamide.

"Alkali metals" are metals found, along with hydrogen, in group I of the periodic table. The alkali metals are lithium, sodium, potassium, rubidium, caesium and francium. It will therefore be understood that an "alkali metal salt" is a chemical compound consisting of an assembly of cations of one or more alkali metals and associated anions.

Accordingly, the term "an alkali metal salt of 4-chloro-N-[2-[(4-chlorophenyl)methyl]-3-oxo-1,2,4-thiadiazol-5-yl]benzamide" refers to a compound comprising alkali metal cations (e.g. lithium, rubidium, caesium and, particularly, sodium and potassium) and anions of 4-chloro-N-[2-[(4-chlorophenyl)methyl]-3-oxo-1,2,4-thiadiazol-5-yl]benzamide. For example, alkali metal salts of 4-chloro-N-[2-[(4-chlorophenyl)methyl]-3-oxo-1,2,4-thiadiazol-5-yl]benzamide may be referred to as the compound of formula II,

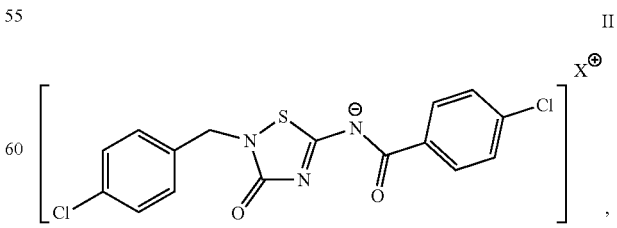

wherein $X^+$ represents the alkali metal (e.g. lithium, rubidium, caesium or, particularly, sodium or potassium) cation.

The skilled person will recognize that, when dissolved in a suitable solvent (e.g. water) the alkali metal salt of 4-chloro-N-[2-[(4-chlorophenyl)methyl]-3-oxo-1,2,4-thiadiazol-5-yl]benzamide may dissociate into its anionic and cationic components.

The compound name 4-chloro-N-[2-[(4-chlorophenyl)methyl]-3-oxo-1,2,4-thiadiazol-5-yl]benzamide was derived using the commercially available software package Autonom (brand of nomenclature software provided as an add-on for use in the Symyx Draw 2.1 ™ office suite marketed by MDL Information Systems).

Throughout this specification, structures may or may not be presented with chemical names. Where any question arises as to nomenclature, the structure prevails. Where it is possible for the compound to exist as a tautomer (e.g. in an alternative resonance form) the depicted structure represents one of the possible tautomeric forms, wherein the actual tautomeric form(s) observed may vary depending on environmental factors such as solvent, temperature or pH. All tautomeric (and resonance) forms and mixtures thereof are included within the scope of the invention. For example, the following tautomers are included within the scope of the invention:

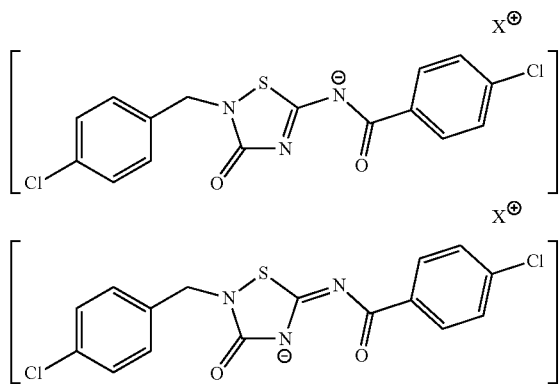

For the avoidance of doubt, alkali metal salts of 4-chloro-N-[2-[(4-chlorophenyl)methyl]-3-oxo-1,2,4-thiadiazol-5-yl]benzamide are solid under ambient conditions, and thus the scope of the invention includes all amorphous, crystalline and pad crystalline forms in thereof.

Alkali metal salts of 4-chloro-N-[2-[(4-chlorophenyl)methyl]-3-oxo-1,2,4-thiadiazol-5-yl]benzamide may be prepared in accordance with techniques that are well known to those skilled in the art. For example, 4-chloro-N-[2-[(4-chlorophenyl)methyl]-3-oxo-1,2,4-thiadiazol-5-yl]benzamide may be reacted with the appropriate alkali metal hydroxide, or an alternative alkali metal base compound. Salt switching techniques may also be used to convert one salt into another salt.

Where the sale is prepared from 4-chloro-N-[2-[(4-chlorophenyl)methyl]-3-oxo-1,2,4-thiadiazol-5-yl]benzamide. 4-chloro-N-[2-[(4-chlorophenyl)methyl]-3-oxo-1,2,4-thiadiazol-5-yl]benzamide may be prepared in accordance with techniques that are well known to those skilled in the art. For example, 4-chloro-N-[2-[(4-chlorophenyl)methyl]-3-oxo-1,2,4-thiadiazol-5-yl]benzamide may be made in accordance with the techniques described in international patent application WO 2011/004162, and all of its content is hereby incorporated by reference.

Unless indicated otherwise, all technical and scientific terms used herein will have their common meaning as understood by one of ordinary skill in the art to which this invention pertains.

In particular embodiments, the alkali metal salt of 4-chloro-N-[2-[(4-chlorophenyl)methyl]-3-oxo-1,2,4-thiadiazol-5-yl]benzamide is a sodium or potassium salt of 4-chloro-N-[2[(4 chlorophenyl)methyl]-3-oxo-1,2,4-thiadiazol-5-yl]benzamide. Preferably, the salt is a sodium salt of 4-chloro-N-[2-[(4-chlorophenyl)methyl]-3-oxo-1,2,4-thiadiazol-5-yl]benzamide. The sodium salt has been found to exhibit a particularly enhanced bioavailability in vivo, as is evidenced by the data in the examples which show that plasma exposure is increased when the active ingredient is administered in this form.

For the avoidance of doubt, the skilled person will understand that references herein to particular aspects of the invention (such as the first aspect of the invention) will include references to all embodiments and particular features thereof, which embodiments and particular features may be taken in combination to form further embodiments and features of the invention.

Salts according to the first aspect of the invention are herein referred to as "salts of the invention".

Pharmaceutical Formulations

As indicated herein, the salts of the invention are useful as therapeutic agents for treating a variety of medical disorders or conditions, Typically, salts of the invention will be administered to a subject in need thereof in the form of a pharmaceutical formulation.

According to a second aspect of the invention, there is provided a pharmaceutical formulation comprising an alkali metal salt (e.g. a sodium salt) of 4-chloro-N-[2-[(4-chlorophenyl)methyl]-3-oxo-1,2,4-thiadiazol-5-yl]benzamide, Such formulations are referred to herein as the formulations of the invention. All embodiments and particular features thereof described herein in respect of the first aspect of the invention are disclosed herein in respect of the second aspect of the invention.

In particular embodiments, the pharmaceutical formulation comprises a salt as defined in the first aspect of the invention, including all embodiments and particular features thereof, wherein said salt has been milled.

The term "milled" (which may be used interchangeably with other terms of the art such as "reduced size", "comminuted", "ground" and "pulverised"), as used herein, refers to a solid sample (e.g. granules) that has been subjected to mechanical energy (e.g. through grinding) to reduce the particle size of the solid sample. For example, coarse particles may be broken down to finer ones, such that the average particle size is reduced.

The phrase "salt has been milled" will be understood to refer to a salt of the invention (as defined in the first aspect of the invention) which has been obtained by any process which involves a step of milling said salt so that the average particle size of the solid salt product is less than the average particle size of a corresponding salt of 4-chloro-N-[2[(4-chlorophenyl)methyl]-3-oxo-1,2,4-thiadiazol-5-yl]benzamide that has been produced by a process known in the art but which has not been processed to reduce its particle size.

Milling is regarded as a 'top-down' approach to the production of fine particles. For example, a drug solid may be cut by sharp blades (e.g. cutter mill), impacted by hammers, subjected to high pressure homogenisation, or crushed or compressed by the application of pressure (e.g. roller-mill or pestle and mortar). As a limited amount of energy is typically imparted, particles produced by such methods remain relatively coarse. Technological advancements in milling equipment have enabled the production of ultrafine drug particles down to micron (i.e. the μm unit range) or even sub-micron (e.g. the nm unit range) dimensions.

Certain milling processes may be characterised as being dry milling processes. Such processes are preferred for processing of the salts of the invention.

'Dry milling' refers to a process in which a drug is milled in its dry state, i.e. in the absence of a liquid medium (e.g. in the substantial absence of water). In the dry state, the drug can be milled alone, or in the presence of one or more other components, such as pharmaceutically acceptable excipients. Other abrasive materials, such as salts, may be present during the milling process to aid in the particle size reduction. The mechanical energy imparted by dry milling fosters interactions between particles of the drug (and optionally other substances present) via van der Waals forces or hydrogen bonding.

A review of milling processes for pharmaceutical products may be found in e.g. Loh et al, Asian Journal of Pharmaceutical Sciences, 10 (2015), 255-274. Excipients suitable for inclusion in drug particles are known in the art, e.g. as described in Peltonen et al., in Handbook of Polymers for Pharmaceutical Technologies, ed. Thakur and Thakur, Wiley, volume 4, chapter 3, 67-87, and Nekkanti et al, in Drug Nanoparticles—An Overview, The Delivery of Nanoparticles, IntechOpen. The content of these documents are incorporated by reference.

The salts and formulations of the invention (as defined by the first and second aspects of the invention, and all embodiments of those aspects) have been found to be surprisingly effective at improving (e.g. increasing) the bioavailability of 4-chloro-N-[2-[(4-chlorophenyl)methyl]-3-oxo-1,2,4-thiadiazol-5-yl]benzamide in vivo compared to a pharmaceutical formulation comprising 4-chloro-N-[2-[(4-chlorophenyl)methyl]-3-oxo-1,2,4-thiadiazol-5-yl]benzamide in the free base form. Improvement in bioavailability may be demonstrated by measuring the $C_{max}$ or the area under the curve (AUC) following administration of the pharmaceutical formulation to an animal, typically a mammal. The salts and formulations of the invention are useful in the therapies described herein in a subject in need of such therapy. Preferably the subject is a human.

In the context of the present invention, the term "free base" refers to a form of 4-chloro-N-[2-[(4-chlorophenyl)methyl]-3-oxo-1,2,4-thiadiazol-5-yl]benzamide which is not in a salt form. For instance, the 4-chloro-N-[2-[(4-chlorophenyl)methyl]-3-oxo-1,2,4-thiadiazol-5-yl]benzamide is not in an ionic (e.g. anionic) form in association with one or more oppositely charged ions (e.g. cations). Free base 4-chloro-N-[2-[(4-chlorophenyl)methyl]-3-oxo-1,2,4-thiadiazol-5-yl]benzamide may be depicted as the compound of formula I,

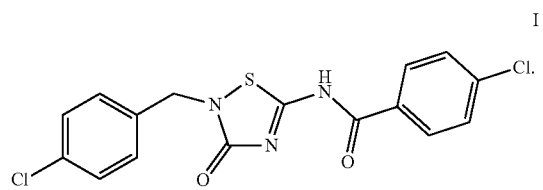 [SMILES: O=C(Nc1nc(=O)n(Cc2ccc(Cl)cc2)s1)c1ccc(Cl)cc1]

I

The terms "$C_{max}$" and "AUC" will be well understood by the person skilled in the art to refer, in the present context, to the peak plasma concentration of 4-chloro-N-[2-[(4-chlorophenyl)methyl]-3-oxo-1,2,4-thiadiazol-5-yl]benzamide after administration (e.g. to a human subject) and the integral of the concentration/time curve for that substance following the administration of the salt or formulation of the invention, respectively.

It has been found that administration of salts of the active ingredient surprisingly resulted in a significant increase in the systemic exposure of 4-chloro-N-[2-[(4-chlorophenyl)methyl]-3-oxo-1,2,4-thiadiazol-5-yl]benzamide as compared to administration of the compound in a non-salt form (i.e. the free form of said compound).

Stabilisers, such as polymers and surfactants, are often used during milling processes in order to increase the repulsion between particles and inhibit aggregation. Aggregation of finely ground particles may occur during micronisation, which can ultimately slow down the dissolution process and affect bioavailability. The increase in the systemic exposure of 4-chloro-N-[2-[(4-chlorophenyl)methyl]-3-oxo-1,2,4-thiadiazol-5-yl]benzamide has been found to occur following administration of dry milled salt of the active ingredient even without the addition of stabilisers. Thus, in one embodiment, the pharmaceutical formulation does not comprise any stabilisers.

Thus, the formulation of second aspect of the invention is capable of increasing the bioavailability of 4-chloro-N-[2-[(4-chlorophenyl)methyl]-3-oxo-1,2,4-thiadiazol-5-yl]benzamide compared to pharmaceutical formulations comprising the free base form of 4-chloro-N-[2-[(4-chlorophenyl)methyl]-3-oxo-1,2,4-thiadiazol-5-yl]benzamide.

When we state "is capable of increasing the bioavailability of 4-chloro-N-[2-[(4-chlorophenyl)methyl]-3-oxo-1,2,4-thiadiazol-5-yl]benzamide compared to pharmaceutical formulations comprising the free base form of 4-chloro-N-[2-[(4-chlorophenyl)methyl]-3-oxo-1,2,4-thiadiazol-5-yl]benzamide", we mean that administration of a formulation comprising the salt of the invention results in a larger systemically available fraction of 4-chloro-N-[2-[(4-chlorophenyl)methyl]-3-oxo-1,2,4-thiadiazol-5-yl]benzamide in vivo compared to administration of a formulation comprising free 4-chloro-N-[2-[(4-chlorophenyl)methyl]-3-oxo-1,2,4-thiadiazol-5-yl]benzamide. The increase in the amount of 4-chloro-N-[2-[(4-chlorophenyl)methyl]-3-oxo-1,2,4-thiadiazol-5-yl]benzamide that is systemically available following administration of a formulation comprising the salt of the invention as compared to administration of a formulation comprising free 4-chloro-N-[2-[(4-chlorophenyl)methyl]-3-oxo-1,2,4-thiadiazol-5-yl]benzamide may be at least about 10%, (at least) about 20%, about 30%, about 40%, about 50%, about 60%, about 70%, about 80%, about 90%, about 100% (i.e. 2-fold), about 150%, about 200% (i.e. 3-fold), about 250%, about 300% (i.e. 4-fold), about 350%, or about 400% (i.e. 5-fold).

The improvement of the bioavailability provided by the formulations of the invention may be demonstrated using suitable methods known in the art. For example, the improvement in bioavailability may be demonstrated by comparing the pharmacokinetic data (e.g. AUC data) for a subject who has been administered a formulation comprising a salt of the invention with the corresponding data for a subject who has been administered a pharmaceutical formulation comprising 4-chloro-N-[2-[(4-chlorophenyl)methyl]-3-oxo-1,2,4-thiadiazol-5-yl]benzamide in the free base form.

Milling reduces the average size of the particles containing the alkali metal salt of 4-chloro-N-[2-[(4-chlorophenyl)methyl]-3-oxo-1,2,4-thiadiazol-5-yl]benzamide. The extent and effectiveness of the milling may be determined by measuring the particle size distribution of said particles before and after the milling process.

The term "particle size distribution" refers to the relative number of particles present according to size in a solid sample, such as a powder, a granular material, or particles dispersed in a fluid. Particle size distribution affects the properties of a solid sample (e.g. a powder, and the like) in many ways. We have found that the reduction of the average particle size results in a surprising improvement in the bioavailability of the resulting pharmaceutical product.

The particle size distribution of a solid sample may be measured using techniques that are well known in the art. For example, the particle size distribution of a solid sample may be measured by laser diffraction, dynamic light scattering, image analysis (e.g. dynamic image analysis), sieve analysis, air elutriation analysis, optical counting, electroresistance counting, sedimentation, laser obscuration and acoustic (e.g. ultrasound attenuation) spectroscopy. Particular methods that may be mentioned for measuring the particle size distribution of particles of the salt of the invention are dynamic light scattering and laser diffraction.

Particle size distributions may be also determined based on results from sieve analysis. Sieve analysis presents particle size information in the form of an S-curve of cumulative mass retained on each sieve versus the sieve mesh size. The most commonly used metrics when describing particle size distributions are D-values (e.g. D10, D50 and D90, which are the intercepts for 10%, 50% and 90% of the cumulative mass, respectively). The particle size distribution of the present invention is preferably defined using one or more of such values. D-values essentially represent the diameter of the sphere which divides the sample's mass into a specified percentage when the particles are arranged on an ascending mass basis. For example, the D10 value is the diameter at which 10% of the sample's mass is comprised of particles with a diameter of less than this value. The D50 value is the diameter of the particle that 50% of a sample's mass is smaller than and 50% of a sample's mass is larger than.

The particles containing a salt of the invention may have a particle size distribution defined by a D90 of less than about 10 µm (e.g. from about 5 µm to about 10 µm). The particles consisting of the salt of the invention may have a particle size distribution defined by a D50 of less than about 6 µm (e.g. from about 1 µm to about 6 µm). The particle size distribution of the particles consisting of the salt of the invention may further be a defined by a D10 of less than about 2 µm (e.g. from about 0.5 µm to about 2 µm). In particular embodiments, the formulation comprises particles containing the salt of the invention, said particles having a particle size distribution defined by a D90 of less than about 10 µm.

The particle size distribution parameters mentioned above may be applicable, individually or in combination, to any given salt, mixture or formulation. For example, in particular embodiments, the formulation comprises particles containing the salt of the invention, said particles having a particle size distribution defined by a D90 of less than about 10 µm and a D50 of less than about 6 µm.

The particle size distribution of particles containing the salt of the invention may be measured by laser diffraction, using, for example a particle size analyser (such as a Shimadzu SALD-2300). Where such a process involves the dispersion of the substance to be analysed in a liquid medium (e.g. water), a suitable amount of a dispersion agent may be used, for example Tween 20 (polyethylene glycol sorbitan monolaurate).

The present invention also encompasses a pharmaceutical formulation comprising particles containing the salt of the invention with any of the particle size distributions defined herein, regardless of the process by which the particles are produced.

Preferably, the pharmaceutical formulation of the second aspect of the invention comprises particles of the salt of the invention with any of the particular particle size distributions described herein, wherein the particles are obtained by a process which involves milling said salt.

The pharmaceutical formulations of the second aspect of the invention may be prepared in accordance with standard and/or accepted pharmaceutical practice.

In an embodiment of the second aspect of the invention, the salt of the invention is the sole active pharmaceutical ingredient present in the particles which contain the salt. In a further embodiment of the second aspect of the invention, the salt of the invention is present in the formulation alongside one or more other active pharmaceutical ingredients, or may be administered as part of a combination therapy with one or more other active pharmaceutical ingredients.

As described herein, formulations of the second aspect invention may, for example, comprise particles containing the salt of the invention which salt has been milled so that the particles have a particle size distribution defined by a D90 of less than about 10 µm.

Thus, according to a third aspect of the invention, there is provided a process for preparing a formulation as defined hereinabove (i.e. a formulation according to the second aspect of the invention, and all embodiments thereof), wherein the process comprises milling the salt of the invention, optionally together with one or more excipients, to produce particles having a particle size distribution defined by a D90 of less than about 10 µm.

In one embodiment of the third aspect of the invention, the particles are milled using dry milling. Dry milling typically involves milling of the substance (i.e. the drug) in the substantial absence of other components (e.g. in the substantial absence of any other components of the pharmaceutical formulation). Thus, in one embodiment, the particles consist essentially of the salt of the invention and have a particle size distribution as defined herein. In another embodiment, the particles consist essentially of the salt of the invention and have been obtained by dry milling.

Optionally, the dry milling involves jet milling. Jet milling is a milling process which involves high velocity compressed air streams in order to reduce the size of drug particles, typically from the range of 20 to 100 µm, down to less than 10 µm. Reduction in particle size is achieved by a combination of impact (either between particles or of particles onto the wall of the milling chamber) and attrition (as particles move against each other). The skilled person would appreciate that control of the particle size can be achieved by varying the milling conditions in accordance with methods that are known in the art.

In particular embodiments of the process of the third aspect of the invention, the salt of 4-chloro-N-[2-[(4-chlorophenyl)methyl]-3-oxo-1,2,4-thiadiazol-5-yl]benzamide is mixed with one or more excipients after milling of the salt of 4-chloro-N-[2-[(4-chlorophenyl)methyl]-3-oxo-1,2,4-thiadiazol-5-yl]benzamide.

In other embodiments of the process of the third aspect of the invention, an enteric coating may be introduced into the formulation at any time point, provided the salt of the invention in the resulting formulation is encapsulated within the enteric coating. For example, when the pharmaceutical formulation is provided in the form of a capsule or tablet, the process may further comprise the step of coating said capsule or tablet with the enteric coating before or after (preferably after) the milled salt of 4-chloro-N-[2-[(4-chlorophenyl)methyl]-3-oxo-1,2,4-thiadiazol-5-yl]benzamide has been incorporated into said capsule or tablet. Alternatively, the process may further comprise the step of applying the enteric coating to the milled salt of 4-chloro-N-[2-[(4-chlorophenyl)methyl]-3-oxo-1,2,4-thiadiazol-5-yl]benzamide prior to the incorporation of said particles into a capsule or tablet.

Dry milling may be useful for producing particles that are generally larger in size than those obtained from wet milling, Particular particle size distributions that may be mentioned in this context include those with a D90 of less than about 10 µm, less than about 9 µm, less than about 8 µm, less than about 7 µm or less than about 6 µm.

More specifically, the particles containing the salt of the invention present in a formulation defined herein may have a particle size distribution defined by a D90 of about 5 µm, about 5.5 µm, about 6 µm, about 6.5 µm, about 7 µm, about 7.5 µm, about 8 µm, about 8.5 µm, about 9 µm, about 9.5 µm or about 10 µm. Said particle size distributions preferably relate to particles that consist essentially of the salt of the invention.

Preferably, the particles containing the salt of the invention have a particle size distribution defined by a D50 of less than about 6 µm, less than about 5 µm, less than about 4 µm, less than about 3 µm, or less than about 2 µm.

The particle size distribution of the particles containing the salt of the invention may also be a defined by a D50 of about 1 µm, about 1.5 µm, about 2 µm, about 2.5 µm, about 3 µm, about 3.5 µm, about 4 µm, about 4.5 µm, about 5, about 5.5 or about 6 µm.

Still further, the particles containing the salt of the invention may have a particle size distribution defined by a D10 of less than about 2 µm, less than about 1.5 µm, or less than about 1 µm.

The particle size distribution of the particles containing the salt of the invention may also 30 be a defined by a D10 of about 0.5 µm, about 1 µm, about 1.5 µm or about 2 µm.

Thus, in a particular embodiment of the formulation (i.e. formulations according to any embodiment of the second aspect of the invention), the particles containing the salt of the invention have a particle size distribution defined by a D90 of less than 9 µm; a D50 of less 35 than 6 µm; a D50 of less than 5 µm, a D10 of less than 2 µm; or a D10 of less than 1.5 µm.

The formulations of the second aspect of the invention will generally be provided as a mixture comprising the salt of the invention and one or more pharmaceutically acceptable excipients. The one or more pharmaceutically acceptable excipients may be selected with due regard to the intended route of administration in accordance with standard pharmaceutical practice. Such pharmaceutically acceptable excipients are preferably chemically inert to the active compound and are preferably have no detrimental side effects or toxicity under the conditions of use. Suitable pharmaceutical formulations may be found in, for example, Remington The Science and Practice of Pharmacy, 19th ed., Mack Printing Company, Easton, Pa. (1995). A brief review of methods of drug delivery may also be found in e.g. Langer, Science 249, 1527 (1990).

It has been found that pH modifying excipients are particularly advantageous in the formulations of the invention, pH modifying excipients are those which substantially alter the pH of an aqueous solution of a formulation compared to the pH of an aqueous solution of the same formulation that does not otherwise comprise said excipients. A pH modifying excipient may raise (or lower) the pH of an aqueous solution of a formulation (e.g. to a pH of 8 or more) compared to an aqueous solution of the same formulation that does not comprise said excipient. Such excipients may be useful for increasing (i.e. improving) the aqueous solubility and/or stability of the compound of the invention in the formulation.

In the formulations of the invention, it has been found that basic excipients are useful in combination with the salts of the inventions and result in an improvement in the solubility of the compound. Thus, in particular embodiments of the second aspect of the invention, the at least one pharmaceutically acceptable excipient is a basic excipient.

As used herein, the term "basic excipient" refers to a pharmaceutically acceptable excipient that increases the microenvironmental pH of the formulation. Modulation of the microenvironmental pH of a formulation has been found to improve the dissolution of the active ingredient in the formulation, which in turn may lead to enhanced oral absorption of the active ingredient. Particular basic excipients that may be mentioned include magnesium oxide, sodium hydrogen carbonate, potassium hydrogen carbonate, sodium carbonate, potassium carbonate, magnesium carbonate and calcium carbonate. In particular embodiments, the basic excipient is magnesium oxide.

Thus, according to particular embodiments, the formulation further comprises at least one pharmaceutically acceptable excipient. In particular, the at least one pharmaceutically acceptable excipient may be a lubricant, a binder, a filler, a surfactant, a diluent, an anti-adherent, a coating, a flavouring, a colourant, a glidant, a preservative, a sweetener, a disintegrant, an adsorbent, a buffering agent, an antioxidant, a chelating agent, a dissolution enhancer, a dissolution retardant or a wetting agent.

Particular pharmaceutically acceptable excipients that may be mentioned include mannitol, PVP (polyvinylpyrrolidone) K30, lactose, saccharose, sorbitol, starch, amylopectin, cellulose derivatives, gelatin, or another suitable ingredients, as well as disintegrating agents and lubricating agents such as Na-docusate, magnesium stearate, calcium stearate, sodium stearyl fumarate and polyethylene glycol waxes. In the preparation of a pharmaceutical formulation of the salt of the invention for oral administration, particles containing the salt of the invention (preferably after milling) may be mixed, either together or separately, with mannitol, PVP (polyvinylpyrrolidone) K30 and Na-docusate Thus, in particular embodiments, the formulation of the invention comprises PVP K30, Na-docusate and mannitol.

Such mixtures may then be processed into pellets or granules, or compressed into tablets. Thus, pharmaceutical formulations of the invention include formulations that are provided in the form of a tablet, mini-tablets, blocks, pellets, particles, granules or a powder for oral administration.

The skilled person will understand that formulations described herein may act systemically, and may therefore be administered accordingly using suitable techniques known to those skilled in the art. Formulations as described herein will normally be administered orally, in a pharmaceutically acceptable dosage form. Thus, the pharmaceutical formulation of the second aspect of the invention is preferably an oral pharmaceutical formulation.

Formulations of the invention may be prepared for oral administration in the form of a capsule. For example, capsules such as soft gelatin capsules may be prepared containing the salt of the invention alone, or together with a suitable vehicle, e.g. vegetable oil, fat etc. Similarly, hard gelatin capsules may contain the salt of the invention alone, or in combination with solid powdered ingredients such as a disaccharide (e.g. lactose or saccharose), an alcohol sugar (e.g. sorbitol or mannitol), a vegetable starch (e.g. potato starch or corn starch), a polysaccharide (e.g. amylopectin or cellulose derivatives) or gelling agent (e.g. gelatin).

Thus, pharmaceutical formulations of the invention include formulations that are provided in the form of a capsule or a tablet, e.g. for oral administration.

Preparations intended for oral administration may further comprise an enteric coating in order to prevent or minimise dissolution or disintegration in the gastric environment. As such, oral preparations (e.g. capsules or tablets) coated by an enteric coating may provide targeted release of the salt of the invention in the small intestine. For example, the enteric coating may be present on surface of the formulation (e.g. on the surface of a tablet or a capsule), or each of the particles containing the salt of the invention may be coated with the enteric coating. Thus, in particular embodiments, the formulation further comprises an enteric coating.

It may be desirable to minimise dissolution or disintegration of a capsule or a tablet (and the like) in the gastric environment and/or provide targeted release of the active ingredient in the small intestine, Thus, in particular embodiments, the enteric coating is present on said capsule or tablet. For example, said coating may be provided as an outer layer on said capsule or tablet.

Alternatively, particles containing the salt of the invention may be individually coated with the enteric coating, and said coated particles may be loaded into a capsule or compressed into a tablet. Thus, in particular embodiments, the capsule or tablet contains particles comprising the salt of the invention and each particle is coated with the enteric coating.

The term "enteric coating" refers to a substance (e.g. a polymer) that is incorporated into an oral medication (e.g. applied onto the surface of a tablet, a capsule, particles or pellets) and that inhibits dissolution or disintegration of the medication in the gastric environment. Enteric coatings are typically stable at the highly acidic pH found in the stomach, but break down rapidly in the relatively basic pH of the small intestine. Therefore, enteric coatings prevent release of the active ingredient in the medication until it reaches the small intestine.

Any enteric coating known to the skilled person may be used in the present invention Particular enteric coating materials that may be mentioned include those which comprise beeswax, shellac, an alkylcellulose polymer resin (e.g. ethylcellulose polymers, carboxymethylethylcellulose, or hydroxypropyl methylcellulose phthalate) or an acrylic polymer resin (e.g. acrylic acid and methacrylic acid copolymers, methacrylic acid copolymers, methyl methacrylate copolymers, ethoxyethyl methacrylates, cyanoethyl methacrylate, methyl methacrylate, copolymers, methacrylic acid copolymers, methyl methacrylate copolymers, methyl methacrylate copolymers, methacrylate copolymers, methacrylic acid copolymer, aminoalkyl methacrylate copolymer, methacrylic acid copolymers, methyl methacrylate copolymers, poly(acrylic acid), poly(methacrylic acid), methacrylic acid alkylamide copolymer, poly(methyl methacrylate), poly (methacrylic acid) (anhydride), methyl methacrylate, polymethacrylate, methyl methacrylate copolymer, poly(methyl methacrylate), poly(methyl methacrylate) copolymer, polyacrylamide, aminoalkyl methacrylate copolymer, poly (methacrylic acid anhydride), glycidyl methacrylate copolymers), cellulose acetate phthalate, and polyvinyl acetate phthalate, A particular polyacrylic resin that may be mentioned is polyacrylic resin HB-50.

Preferably, the pharmaceutical formulation of the second aspect of the invention comprises milled particles of the salt of the invention, said particles having any of the particular particle size distributions described herein, and wherein the formulation further comprises an enteric coating. Thus, in particular embodiments, in the pharmaceutical formulation of the second aspect of the invention the salt of 4-chloro-N-[2-[(4-chlorophenyl)methyl]-3-oxo-1,2,4-thiadiazol-5-yl] benzamide has been milled so that particles containing the salt have a particle size distribution defined by a D90 of less than 10 μm, and the formulation further comprises an enteric coating.

Pharmaceutical formulations that may be mentioned include those in which the salt of the invention is present in a total amount that is at least 1% (or at least 10%, at least 30% or at least 50%) by weight of the formulation. That is, the weight ratio of the salt of the invention to the totality of the components (i.e. the salt of the invention and all pharmaceutical excipients, e.g. adjuvants, diluents and carriers) of the pharmaceutical formulation is at least 1:99 (or at least 10:90, at least 30:70 or at least 50:50).

A "therapeutically effective amount", an "effective amount" or a "dosage" as used herein refers to an amount of a salt of the invention that is sufficient to produce a desired effect, which can be a therapeutic and/or beneficial effect. The effective amount or dosage will vary with the age or general condition of the subject (e.g. a human), the severity of the condition being treated, the particular agents administered, the duration of the treatment, the nature of any concurrent treatment, the pharmaceutically acceptable carrier used, and like factors within the knowledge and expertise of those skilled in the art. As appropriate, a "therapeutically effective amount" "effective amount" or "dosage" in any individual case can be determined by one of skill in the art by reference to the pertinent texts and literature and/or by using routine experimentation. Those skilled in the art will appreciate that the therapeutic effects need not be complete or curative, as long as some benefit is provided to the subject.

The skilled person will understand that formulations of the invention may be administered (for example, by way of one or more preparations as described herein) at varying doses, with suitable doses being readily determined by one of skill in the art. The total dosage of the salt of the invention that is to be administered to a subject in need thereof may range from about 0.01 to about 2000 mg/kg of body weight per day (mg/kg/day), about 0.1 to about 500 mg/kg/day, or about 1 to about 100 mg/kg/day. Such dosages may be, for example, oral dosages of the formulations of the second aspect of the invention.

When administered orally, treatment with such formulations (including capsules containing such formulations) may comprise administration of a unit dose formulation containing from about 0.01 mg to about 3000 mg of the salt of the invention, for example from about 0.1 mg to about 2000 mg, or from about 1 mg to about 1000 mg (e.g. from about 10 mg to about 500 mg), of the salt of the invention. Advantageously, treatment may comprise administration of the salt of the invention (including capsules containing said formulation) using a single daily dose. Alternatively, the total daily dosage of the salt of the invention may be administered in divided doses two, three or four times daily (e.g. twice daily with reference to the doses described herein, such as a dose of 100 mg, 250 mg, 500 mg or 1000 mg twice daily). The skilled physician will recognise that the dosage will vary from subject to subject.

In particular embodiments, the daily dose of the salt of the invention administered to a subject is in the range of from about 1 to about 3000 mg, preferably from about 1 to about 1000 mg.

The term "about," as used herein when referring to a measurable value such as an amount of a compound, dose, time, temperature, and the like, refers to variations of 20%, 10%, 5%, 1%, 0.5%, or even 0.1% of the specified amount. It is contemplated that, at each instance, such terms may be replaced with the notation "±10%", or the like (or by indicating a variance of a specific amount calculated based on the relevant value). It is also contemplated that, at each instance, such terms may be deleted.

For the avoidance of doubt, the dose administered to a subject, particularly a human subject, in the context of the present invention should be sufficient to effect a therapeutic response in the subject over a reasonable timeframe. One skilled in the art will recognize that the selection of the exact dose and composition and the most appropriate delivery regimen will also be influenced by inter ala the pharmacological properties of the formulation, the nature and severity of the condition being treated, and the physical condition and mental acuity of the recipient, as well as the potency of the specific compound, the age, condition, body weight, sex and response of the subject to be treated, and the stage/severity of the disease.

In any event, the medical practitioner, or other skilled person, will be able to determine routinely the actual dosage which will be most suitable for an individual subject. The above-mentioned dosages are exemplary of the average case; there can, of course, be individual instances where higher or lower dosage ranges are merited, and such are within the scope of this invention.

Medical Uses

The salt of the invention, and formulations thereof, are useful as pharmaceuticals. The salt the invention (i.e. a salt as defined in the first aspect of the invention, including all embodiments and particular features thereof), and formulations thereof (i.e. a formulation as defined in the second of the invention, including all embodiments and particular features thereof), may be particularly useful in treating a disorder or condition ameliorated by the activation of AMP-activated protein kinase (AMPK). Thus, in a fourth aspect of the invention, there is provided the use of a salt of the invention, or a formulation comprising said salt, as defined herein, in the manufacture of a medicament for the treatment of a disorder or condition ameliorated by the activation of AMPK.

Similarly, there is provided a method of treating a disorder or condition ameliorated by the activation of AMPK comprising administering to a subject (e.g. a human) in need thereof a therapeutically effective amount of a salt of the invention or a formulation comprising said salt. Likewise, there is provided the salt of the invention (or a formulation comprising said salt) for use in a method of treating a disorder or condition ameliorated by the activation of AMPK.

By 'activate AMPK', we mean that the steady state level of phosphorylation of the Thr-172 moiety of the AMPK-α subunit is increased compared to the steady state level of phosphorylation in the absence of 4-chloro-N-[2-[(4-chlorophenyl)methyl]-3-oxo-1,2,4-thiadiazol-5-yl]benzamide. Alternatively, or in addition, we mean that there is a higher steady state level of phosphorylation of any other proteins downstream of AMPK, such as acetyl-CoA carboxylase (ACC).

The terms "disorder or condition ameliorated by the activation of AMPK" will be understood by those skilled in the art to include cancer, diabetes, cardiovascular diseases, hyperinsulinemia and associated conditions, a condition/disorder where fibrosis plays a role, sexual dysfunction, osteoporosis and neurodegenerative diseases.

The term "cancer" will be understood by those skilled in the art to include one or more diseases in the class of disorders that is characterized by uncontrolled division of cells and the ability of these cells to invade other tissues, either by direct growth into adjacent tissue through invasion, proliferation or by implantation into distant sites by metastasis. By "proliferation" we include an increase in the number and/or size of cancer cells. By "metastasis" we mean the movement or migration (e.g. invasiveness) of cancer cells from a primary tumor site in the body of a subject to one or more other areas within the subject's body (where the cells can then form secondary tumors), 4-Chloro-N-[2-[(4-chlorophenyl)methyl]-3-oxo-1,2,4-thiadiazol-5-yl]benzamide is capable of inhibiting the proliferation of cancer cells and the metastasis of cancer cells.

Thus, formulations of the invention may be suitable for use in the treatment of any cancer type, including all tumors (non-solid and, preferably, solid tumors, such as carcinoma, adenoma, adenocarcinoma, blood cancer, irrespective of the organ). For example, the cancer cells may be selected from the group consisting of cancer cells of the breast, bile duct, brain, colon, stomach, reproductive organs, thyroid, hematopoietic system, lung and airways, skin, gallbladder, liver, nasopharynx, nerve cells, kidney, prostate, lymph glands and gastrointestinal tract. Preferably, the cancer is selected from the group of colon cancer (including colorectal adenomas), breast cancer (e.g. postmenopausal breast cancer), endometrial cancer, cancers of the hematopoietic system (e.g. leukemia, lymphoma, etc.). thyroid cancer, kidney cancer, oesophageal adenocarcinoma, ovarian cancer, prostate cancer, pancreatic cancer, gallbladder cancer, liver cancer and cervical cancer. More preferably, the cancer is selected from the group of colon, prostate and, particularly, breast cancer. Where the cancer is a non-solid tumor, it is preferably a hematopoietic tumor such as a leukemia (e.g. Acute Myelogenous Leukemia (AML), Chronic Myelogenous Leukemia (CML), Acute Lymphocytic Leukemia (ALL). Chronic Lymphocytic Leukemia (CLL). Preferably the cancer cells are breast cancer cells.

The term "diabetes" (i.e. diabetes mellitus) will be understood by those skilled in the art to refer to both type 1 (insulin-dependent) diabetes and type 2 (insulin-independent) diabetes, both of which involve the malfunction of glucose homeostasis. The salts of the invention and formulations thereof may be particularly suitable for use in the treatment of type 1 diabetes and/or type 2 diabetes.

The term "hyperinsulinemia or an associated condition" will be understood by those skilled in the art to include hyperinsulinemia, type 2 diabetes, glucose intolerance, insulin resistance, metabolic syndrome, dyslipidemia, hyperinsulinism in childhood, hypercholesterolemia, high blood pressure, obesity, fatty liver conditions, diabetic nephropathy, diabetic neuropathy, diabetic retinopathy, cardiovascular disease, atherosclerosis, cerebrovascular conditions such as stroke, systemic lupus erythematosus, neurodegenerative diseases such as Alzheimer's disease, and polycystic ovary syndrome, Other disease states include progressive renal disease such as chronic renal failure.

In particular, salts of the invention and formulations thereof may be suitable for use in the treatment of obesity associated with hyperinsulinemia and/or cardiovascular disease associated with hyperinsulinemia.

Salts of the invention and formulations thereof may also be suitable for use in the treatment of cardiovascular disease, such as heart failure, wherein said cardiovascular disease is not associated with hyperinsulinemia. Similarly, salts of the invention and formulations thereof may also be suitable for use in the treatment of obesity which is not associated with hyperinsulinemia. For the avoidance of doubt, the treatment of obesity and/or cardiovascular disease (such as heart failure) where AMPK activation may be beneficial is included within the scope of the invention.

A condition/disorder where fibrosis plays a role includes (but is not limited to) scar healing, keloids, scleroderma, pulmonary fibrosis (including idiopathic pulmonary fibrosis), nephrogenic systemic fibrosis, and cardiovascular fibrosis (including endomyocardial fibrosis), systemic sclerosis, liver cirrhosis, eye macular degeneration, retinal and vitreal retinopathy, Crohn's/inflammatory bowel disease, post-surgical scar tissue formation, radiation and chemotherapeutic-drug induced fibrosis, and cardiovascular fibrosis.

The salt of invention may also be useful in the treatment of sexual dysfunction (e.g. the treatment of erectile dysfunction). The salt of invention may also be useful in the treatment of inflammation.

Neurodegenerative diseases that may be mentioned include Alzheimer's disease, Parkinson's disease and Huntington's disease, amyotrophic lateral sclerosis, polyglutamine disorders, such as spinal and bulbar muscular atrophy (SBMA), dentatorubral and pallidoluysian atrophy (DR-PLA), and a number of spinocerebellar ataxias (SCA).

The skilled person will understand that references to the "treatment" of a particular condition (or, similarly, to "treating" that condition) will take their normal meanings in the field of medicine. In particular, the terms may refer to achieving a reduction in the severity and/or frequency of occurrence of one or more clinical symptom associated with the condition, as judged by a physician attending a subject having or being susceptible to such symptoms.

As used herein, references to a subject (or to subjects) refer to a living subject being treated, or receiving preventative medicine, including mammalian (e.g. human) subjects. In particular, references to a subject refer to a human subject.

The skilled person will understand that such treatment or prevention will be performed in a subject in need thereof. The need of a subject for such treatment or prevention may be assessed by those skilled the art using routine techniques.

In the context of the present invention, a "subject in need" of the salt of the invention includes a subject that is suffering a disorder or condition ameliorated by the activation of AMPK.

As used herein, the terms "disease" and "disorder" (and, similarly, the terms condition, illness, medical problem, and the like) may be used interchangeably.

Without wishing to be bound by theory, it is believed that the administration of 4-chloro-N-[2-[(4-chlorophenyl) methyl]-3-oxo-1,2,4-thiadiazol-5-yl]benzamide in the form of a salt of the invention enhances the bioavailability of 4-chloro-N-[2-[(4-chlorophenyl)methyl]-3-oxo-1,2,4-thiadiazol-5-yl]benzamide in the systemic circulation. Formulations comprising a salt of the invention have been shown to provide an approximately two-fold increase in the bioavailability of the 4-chloro-N-[2-[(4-chlorophenyl)methyl]-3-oxo-1,2,4-thiadiazol-5-yl]benzamide under certain circumstances compared to a formulation that comprises 4-chloro-N-[2-[(4-chlorophenyl)methyl]-3-oxo-1,2,4-thiadiazol-5-yl]benzamide in the free base form.

Salts of the invention (and formulations thereof) may have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, other therapies known in the prior art, whether for use in the above-stated indications or otherwise. In particular, formulations of the invention may have the advantage that they are more efficacious and/or exhibit advantageous properties in vivo.

FIGURES

The following drawings are provided to illustrate various aspects of the present inventive concept and are not intended to limit the scope of the present invention unless specified herein.

FIG. 1 shows comparative results of oral pharmacokinetic studies using 4-chloro-N-[2-[(4-chlorophenyl)methyl]-3-oxo-1,2,4-thiadiazol-5-yl]benzamide (Compound 1) in a suspension and in non-coated capsules, and 4-chloro-N-[2-[(4-chlorophenyl)methyl]-3-oxo-1,2,4-thiadiazol-5-yl]benzamide sodium salt (Compound 2) and 4-chloro-N-[2-[(4-chlorophenyl)methyl]-3-oxo-1,2,4-thiadiazol-5-yl] benzamide potassium salt (Compound 3) separately in non-coated capsules.

EXAMPLES

Figure 1:
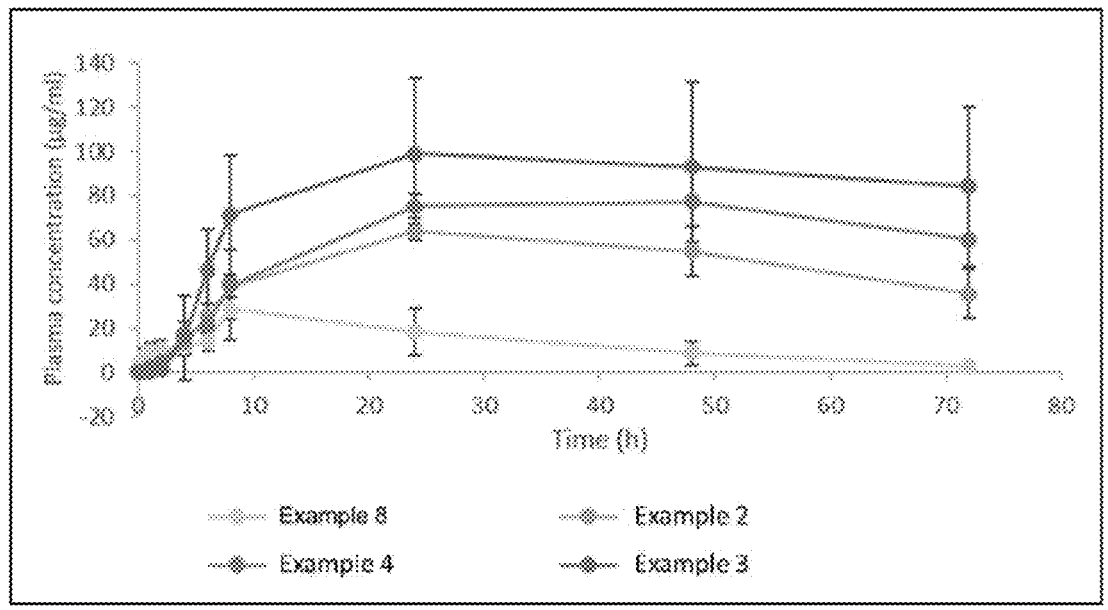

Abbreviations $AUC_{0-t}$: Area under the concentration-time curve from time zero to last quantifiable concentration
$AUC_{0-\infty}$: Area under the concentration-time curve from time zero to infinity
b.w.: Body weight
CE: Collision energy
CL: Clearance
$C_{max}$: Peak plasma concentration.
CXP: Collision exit potential
DLS: Dynamic light scattering DP: Declustering potential
EP Entrance potential
h: Hours
HPLC: High performance liquid chromatography
ISD: Internal standard
$K_2$EDTA Dipotassium ethylene diamine tetra acetic acid
LC: Liquid chromatography
LC-MS/MS: Liquid chromatography—(tandem) mass spectrometry
LS: Light scattering
MRT: Mean residence time.
min: Minutes
PVP K30: Polyvinylpyrrolidone K 30
rpm: Revolutions per minute
RT: Room temperature
$Tv_{1/2}$: Half-life
$T_{max}$: Time to reach the peak plasma concentration
v/v: Volume by volume
w/v: Weight per volume The present invention will be further described by reference to the following examples, which are not intended to limit the scope of the invention.

Materials

4-Chloro-N-[2-[(4-chlorophenyl)methyl]-3-oxo-1,2,4-thiadiazol-5-yl]benzamide (compound 1), 4-chloro-N-[2-[(4-chlorophenyl)methyl]-3-oxo-1,2,4-thiadiazol-5-yl]benzamide sodium salt (compound 2) and 4-chloro-N-[2-[(4-chlorophenyl)methyl]-3-oxo-1,2,4-thiadiazol-5-yl]benzamide potassium salt (compound 3) were prepared by Anthem Biosciences.

Sodium-docusate, PVP K30 and mannitol were supplied by Sigma-Aldrich.

Preparation 1—4-chloro-N-[2-[(4-chlorophenyl)methyl]-3-oxo-1,2,4-thiadiazol-5-yl]benzamide Sodium Salt (Compound 2)

Scheme

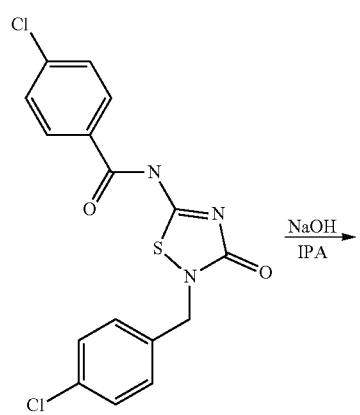

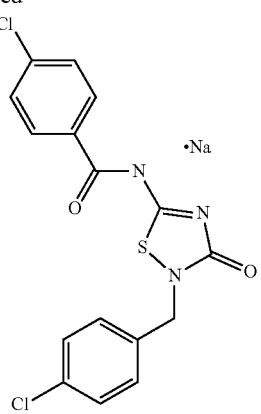

Procedure:

To a suspension of 4-chloro-N-[2-[(4-chlorophenyl)methyl]-3-oxo-1,2,4-thiadiazol-5-yl]benzamide (100 g, 0.2629 mol) in isopropanol (1.0 L) was added slowly a solution of sodium hydroxide (11.56 g, 0.2891 mol) in water (100 mL) at 25±5° C. The mass was stirred for 3 h at 25±5° C. and cooled to 5±5° C. The mass was stirred for 3 h at 5±5° C. and filtered to collect the solids. The solids were washed with isopropanol (300 mL) and dried for 8 h under reduced pressure at 35±5° C. The dried solids were micronized twice using an air jet mill with 4.0 kg/cm² of primary pressure, 7.0 kg/cm² of secondary pressure and screw feeder with 8 RPM to isolate the desired sodium salt as white solid (50 g, 48%).

Preparation 2—4-chloro-N-[2-(4-chlorophenyl)methyl-3-oxo-1,2,4-thiadiazol-5-yl]benzamide Potassium Salt (Compound 3)

Scheme

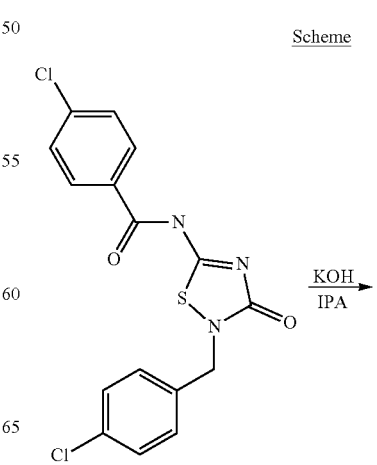

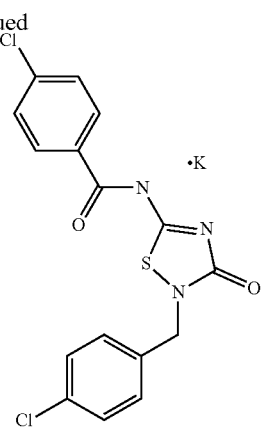

Procedure:

To a suspension of 4-chloro-N-[2-[(4-chlorophenyl) methyl]-3-oxo-1,2,4-thiadiazol-5-yl]benzamide (100 g, 0.2629 mol) in isopropanol (1.0 L) was added slowly a solution of potassium hydroxide (16.22 g, 0.2891 mol) in water (100 mL) at 25±5° C. The mass was stirred for 3 h at 25±5° C. and cooled to 5±5° C. The mass was stirred for 3 h at 5±5° C. and filtered to collect the solids. The solids were washed with isopropanol (300 mL) and dried for 8 h under reduced pressure at 35±5° C. The dried solids were micronized twice using an air jet mill with 4.0 kg/cm² of primary pressure, 7.0 kg/cm² of secondary pressure and screw feeder with 8 RPM to isolate the desired potassium salt as white solid (55 g, 50%).

Example 1—Milled Products

Milling was performed for Examples 1a to 1c using an air jet mill (Equipment code: CP-AJM-01; Promas engineers) with the following parameters:

| Parameter | Value |
| --- | --- |
| Primary pressure (argon/nitrogen) | 4.0 kg/cm² |
| Secondary pressure (argon/nitrogen) | 7.0 kg/cm² |
| Screw feeder RPM | 8 |

Micronisation was repeated in all examples by performing the air jet milling for a second time using the same parameters. This allowed the particle size D90 to be reduced to less than 10 μm.

Particle Size Analysis

Reagents

| Name | Grade |
| --- | --- |
| Water | HPLC |
| Tween 20 | Laboratory Reagent |

Instrument

| Balance | Analytical balance |
| --- | --- |
| Particle size Analyzer | Shimadzu SALD-2300 |

Method Parameter

| Dispersion method | Flow Cell measurement technique with sampler |
| --- | --- |
| Refractive Index | 3.00-0.20i (nearly equal to Fraunhofer) |
| Dispersion Agent | Tween 20 |
| Pump Speed | 5.0 |
| Time of sonication | 10 |
| Blank | 4 drops of Tween 20 in 25 mL water |

Preparations

Four drops of Tween 20 were added to 25 mL of water and the mixture was sonicated for 3 minutes to form the dispersant solution.

0.05 g of milled material was transferred into a 250 mL glass beaker. 25 mL of the dispersant solution (Tween 20/water mixture) was added to the beaker with continuous swirling for 2 to 3 minutes. The suspension was transferred into the measuring unit and the particle size distribution measurements were conducted in triplicate.

TABLE 1

Average particle size results for dry-milled products

| Compound No. | Example No. | Milling | Particle size distribution (μm) | | | |
| --- | --- | --- | --- | --- | --- | --- |
| | | | D10 | D50 | D90 | D100 |
| 1 | Example 1a | Before milling | 13.5 | 28.0 | 55.2 | 187.0 |
| | Example 1b | After 1$^{st}$ milling | 1.8 | 5.0 | 11.4 | 33.7 |
| | Example 1c | After 2$^{nd}$ milling | 1.2 | 3.7 | 8.3 | 21.4 |
| 2 | Example 1d | Before milling | 1.11 | 7.62 | 31.7 | 185 |
| | Example 1e | After 1$^{st}$ milling | 0.508 | 3.58 | 11.5 | 31.1 |
| | Example 1f | After 2$^{nd}$ milling | 0.414 | 2.70 | 8.29 | 24.0 |
| 3 | Example 1g | Before milling | 0.876 | 13.4 | 205 | 665 |
| | Example 1h | After 1$^{st}$ milling | 0.382 | 3.64 | 26.2 | 584 |
| | Example 1i | After 2$^{nd}$ milling | 0.289 | 1.57 | 11.7 | 35.3 |

Examples 2 to 8—Single Dose Oral Pharmacokinetic Studies in Rabbits

The studies detailed below (and referred to as Examples 2 to 8) were conducted to provide comparative single dose oral pharmacokinetics data for Compound 1, as well as sodium and potassium salts of that compound, using non-coated and enteric-coated capsules in male New Zealand White rabbits, Formulation Preparation 1. Capsules Ready to use enteric coated and non-coated capsules were used. Capsules were obtained from CapsulCN International Co., Ltd.

Compound 1 was made using the process described in WO 2011/004162 and milled as described for Example 1c. The non-coated or enteric coated gelatin capsules were individually filled with 180 mg of dry-milled Compound 1 together with accompanying excipients as indicated. Both capsule types were filled with Compound 1 together with 1.8 mg of sodium docusate, 0.18 mg of PVP K30 and 9 mg of mannitol.

Similarly, Compound 2, non-coated or enteric coated gelatin capsules were individually filled with 180 mg of dry-milled Compound 2 (as obtained in Example 1f) together with 1.8 mg of sodium docusate, 0.18 mg of PVP K30 and 9 mg of mannitol.

For Compound 3, non-coated or enteric coated gelatin capsules were individually filled with 90 mg of dry-milled Compound 3 (as obtained in Example 1i) together with 0.90 mg of sodium docusate, 0.09 mg of PVP K30 and 4.50 mg of mannitol.

Once prepared, the capsules were stored in a desiccator at between 19 and 25° C. prior to administration to the animals.

Details of the formulations are summarized in Table 2.

2. Suspensions

Compound 1 was made using the process described in WO 2011/004162.

A 2% w/v methylcellulose solution in 4 mM phosphate buffer pH 7.4 was prepared.

40 mL of the 2% w/v methyl cellulose solution was added to a 250 mL conical flask together with 10 g of 2 mm glass beads, and vigorously stirred. Compound 1 (720 mg) was slowly added to the solution and the mixture was with continuously stirred for 1 h. The so homogenate was transferred to separate flask and its pH recorded. The suspension formulation was prepared before administration to the animals.

Animal Husbandry

Rabbits (New Zealand white; male) were housed under standard laboratory conditions, in environmentally monitored air-conditioned room with adequate fresh air supply (10-15 air changes per hour), room temperature (22±3° C.) and relative humidity 30 to 70%, with 12-hour light and 12-hour dark cycle. The temperature and relative humidity were recorded once daily.

Each animal was housed in a standard stainless steel rabbit cage SS-304 (Size: L 24"×B 18"×H 18") with stainless steel mesh and removable bottom tray for refuse disposal, food hopper for holding pelleted food, holder for drinking water bottle and siphon tube and label holder. Clean, sterilized corncob was provided as bedding material.

The animals were fed ad libitum throughout the acclimatization and experimental periods, with Krishna Valley Agrotech rabbit feed.

Water was provided ad libitum throughout the acclimatization and experimental periods Water from an Aqua guard water filter cum purifier was autoclaved and provided in polypropylene water bottles with stainless steel sipper tubes.

Acclimatization

The animals were acclimatized for a minimum period of 1 weeks (7 days) to facility room conditions and observed for clinical signs daily. Veterinary examination of all the animals were performed on the day of receipt, daily and on the day of randomization.

Grouping

Animal grouping was done by the method of body weight stratification and randomization. The animals selected for the study were weighed and grouped in to body weight ranges. These body weight stratified rabbits were distributed to all the study groups in equal numbers if possible, such that body weight variation of animals used does not exceed ±20% of the mean body weight. The grouping was done one day prior to the initiation of treatment.

Study Design

TABLE 2

| | | | | | | |
|---|---|---|---|---|---|---|
| | | | Study Design | | | |
| Example | No of animals per group | Compound no. | Vehicle | Dose (mg/kg b.w.) | Dose Volume | Concentration of compound |
| 2 | 3 | 1 | Non-coated capsules | 90 | 1 capsule per animal | 180 mg per capsule |
| 3 | 3 | 2 | Non-coated capsules | 90 | 1 capsule per animal | 180 mg per capsule |
| 4 | 3 | 3 | Non-coated capsules | 90 | 2 capsules per animal | 90 mg per capsule |
| 5 | 3 | 1 | Enteric-coated capsules | 90 | 1 capsule per animal | 180 mg per capsule |
| 6 | 3 | 2 | Enteric-coated capsules | 90 | 1 capsule per animal | 180 mg par capsule |
| 7 | 3 | 3 | Enteric-coated capsules | 90 | 2 capsules per animal | 90 mg per capsule |
| 8 | 3 | 1 | Standard suspension | 90 | 5 mL/kg b.w. | 18 mg/mL |

Dose Administration

Adult healthy male New Zealand white rabbits aged approximately 2 to 3 months old were used for experimentation after 7 days of acclimatization.

1. Capsules

To dose the filled capsules, a soft plastic dosing tube was used. The filled capsule was inserted into the dosing tube so that the short end of the capsule protrudes slightly from the tip of the tube. The tip of the capsule was dipped in mineral oil to aid swallowing.

The head was grasped firmly with one hand about the maxilla. The dosing tube containing the capsule was inserted behind the incisors. The dosing tube was slid straight into the back of the mouth. The capsule was ejected by pushing the plunger on the dosing tube. The dosing tube was removed, and the rabbit's mouth was closed. The neck was stroked gently to facilitate swallowing.

2. Suspension

To dose the suspension, an infant feeding tube was used. The feeding tube was inserted through the mouth of the rabbit to the oesophagus and the stomach, and ascertained that it has not been placed in the trachea before dosing to the animals. The suspension of the Compound 1 was administered through the feeding tube. After the administration of the suspension, drinking water of approximately 2.0-2.5 mL was administered to flush out the contents in the feeding tube.

Blood Sampling

The animals were restrained in a rabbit restrainer and blood samples (400-500 μL/time point) were collected via the central ear artery at 0.16, 0.25, 0.50, 1.0, 2.0, 4.0, 6.0, 8.0, 24.0, 48.0 and 72 hours post-dosing. Collected blood specimens were centrifuged at 4000 or 6000 rpm, 4° C. for 10 minutes and plasma samples were separated and stored at ~80° C. until analysis.

Bioanalysis

Concentrations of the analyte of Compound 1 in New Zealand white rabbits was determined using an API 3200 Q-trap LC-MS/MS system.

Method Summary

Chromatographic separation was achieved on Zorbax G18, 50×4.6 mm, 5 µm column with methanol-0.1% formic acid as mobile phase with gradient elution. The flow rate was set at 1.0 mL min$^{-1}$. Detection was accomplished by a triple-quadrupole tandem mass f spectrometer in multiple-reaction monitoring (MRM) scanning via electrospray ionization source, applied in the positive mode. The optimised mass transition ion-pairs for quantitation were m/z 379.999→125.000 for the compound 1 and m/z 376.165→165.00 for the ISD (Haloperidol). Calibration plots were linear over the range of 11.062 to 20594.820 ng/mL.

Buffer (0.1% Formic Acid)

About 1.0 mL of formic acid was added to 999 mL of ultrapure water type-1 to make the buffer. This solution was stored at room temperature and used within two days from the date of preparation.

Dilution Solvent (Methanol:Water. 80:20% v/v)

Exactly 800 mL of methanol and 200 mL of ultrapure water type-1 were added to a reagent bottle, mixed well, and sonicated. This solution was stored at room temperature and used within seven days from the date of preparation.

Rinsing Solvent (Methanol:Water, 50:50% v/v)

Exactly 500 mL of methanol and 500 mL of ultrapure water type-1 were added to a reagent bottle, mixed well, and sonicated. This solution was stored at room temperature and used within three days from the date of preparation.

Preparation of Compound 1 Stock Solution 3.044 mg of compound 1 was weighed, transferred into a 5.0 mL volumetric flask and dissolved in 5 mL of methanol to obtain a 605.756 µg/mL stock solution. The final concentration of compound 1 was corrected according to the potency of the standard and the actual amount weighed.

Internal Standard Stock Solution

About 2.00 mg of Haloperidol (Sigma-Aldrich) was weighed, transferred into a 5.0 mL volumetric flask and dissolved in methanol to obtain a 400 µg/mL internal standard stock solution. The final concentration of Haloperidol was corrected according to the potency of the standard.

Preparation of Internal Standard (Haloperidol) Working Solution

About 0.250 mL of the internal standard stock solution was diluted to 10 mL using a dilution solvent (methanol/water, 80:20) to obtain about approximately 10 µg/mL solution.

Preparation of Calibration Curve for Compound 1 in Plasma

Calibration curve standards were prepared in a range between 11.062-20594.820 ng/mL (Prepared concentrations: 11.062, 20.112, 40.224, 80.449, 160.897, 321.794, 643.588, 1287.176, 2574.353, 5148.705, 10297.410 and 20594.820 ng/mL) in plasma by spiking blank plasma with aqueous analyte standards.

Quality control samples LQC, MQC and HOC falling in the calibration curve range were prepared for Compound 1 (prepared concentrations: 40.224, 5148.705 and 10297.410 ng/mL) in plasma by spiking blank plasma with suitable aqueous analyte standards.

Liquid-Liquid extraction method for plasma samples

10 µL of ISD working solution (approx. 10 µg/mL) was added to an RIA vial.

Exactly 50 µL of rabbit plasma was added from a polypropylene capped tube/vial into the RIA vial and vortexed for 30-40 seconds.

2.5 mL of TBME was added to the RIA vial and then vortexed for 10 minutes at 2000 rpm using a vibramax shaker, The samples were centrifuged at 4000 rpm for 10 minutes at 4° C.

2 mL of organic layer was separated and evaporated to dryness for 20 minutes at 50° C. using a turbo evaporator.

The sample residues were reconstituted with 200 µL of reconstitution solvent (methanol).

The reconstituted samples were then transferred into auto sampler vials.

10 µL of the reconstituted sample was injected into the AR 3200 Q Trap LC-MS/MS system.

Instrumentation Conditions

LC Parameters

Column: Zorbax C18, 50×4.6 mm, 5 µm

Mobile phase: Methanol (A): 0.1% Formic acid (B)

Separation mode: Gradient Mode

Flow rate: 1.0 mL/min

Injection volume: 10 µL

Auto sampler temperature: 10° C.

Column oven temperature: 40° C.

LC-MS/MS API 3200 QTRAP

Source Turbo Ion Spray

Polarity Positive

Scan type MRM m/z of analyte (Compound 1) [M+1] 379.999/125.000 m/z of internal standard (Haloperidol) 376.165/165.000 [M+1]

Ion Spray Voltage (IS) 5500

Temperature (TEM) 500

| Compound name | DP | CE | EP | CXP |
|---|---|---|---|---|
| Compound 1 | 66 | 25 | 4.5 | 16 |
| Haloperidol | 21 | 33 | 7 | 20.676 |

Data Analysis

The data of plasma concentration to respective time points for the analyte Compound 1 were used for the pharmacokinetic analysis. Pharmacokinetic analysis was performed using non-compartmental analysis (NCA) module of Phoenix WinNonlin 6.3 software to in determine the following pharmacokinetic parameters:

$C_{max}$ $T_{max}$ $AUC_{0-t}$ $AUC_{0-\infty}$ $T_{1/2}$:

MRT

Chromatograms of data acquired using the Analyst software version 1.6.1. were processed by the peak area ratio method. 1/×2 was used as the weighting factor. The concentration of the unknown is calculated from the following equation.

$$y = mx + c$$

Where, x=concentration of drug;

m=slope of calibration curve;

y=peak area ratio; and c=intercept of the calibration curve.

Results

Figure 2:
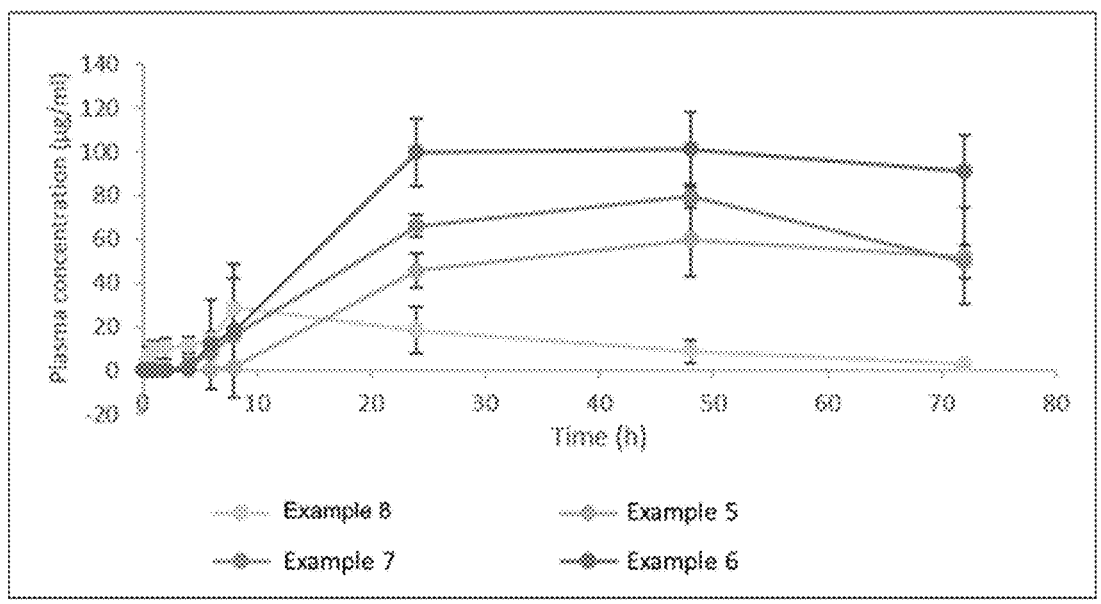
FIG. 2 shows comparative results of oral pharmacokinetic studies using Compound 1 in a suspension and in enteric coated capsules, and Compound 2 and Compound 3 separately in enteric coated capsules.
Figure 3:
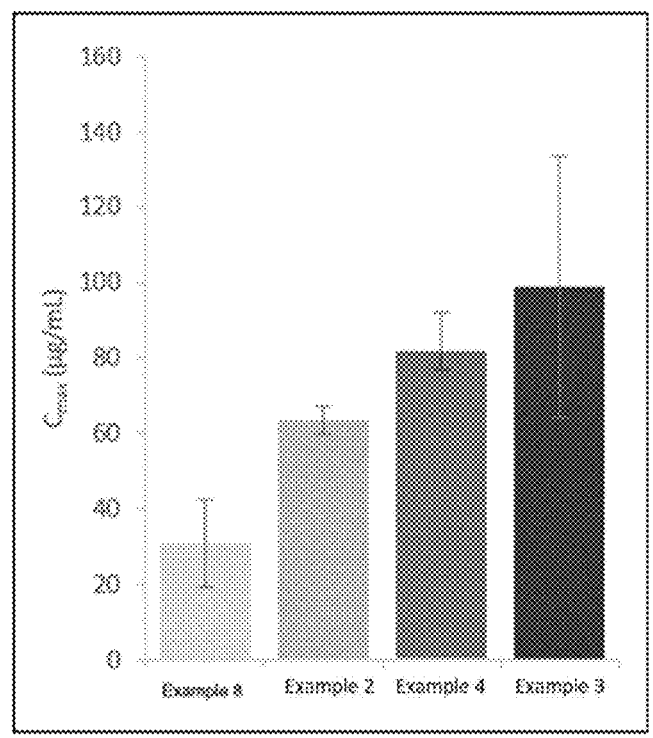
FIGS. 3 and 4 show absolute and relative $C_{max}$ results for formulations of Compound 1 as a suspension and in non-coated capsules, and Compound 2 and Compound 3 separately in non-coated capsules.
Figure 4:
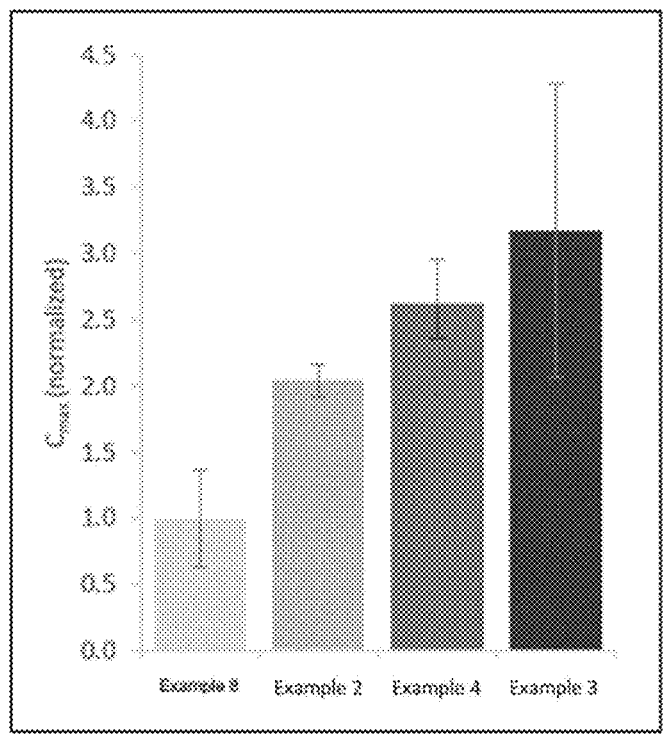
Figure 5:
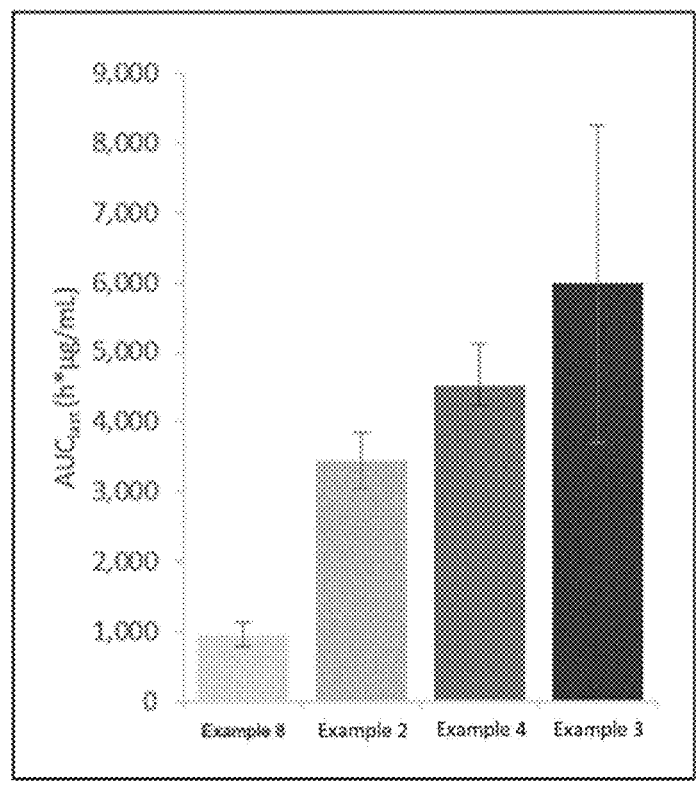
FIGS. 5 and 6 show absolute and relative AUC results for formulations of Compound 1 as a suspension and in non-coated capsules, and Compound 2 and Compound 3 separately in non-coated capsules.
Figure 6:
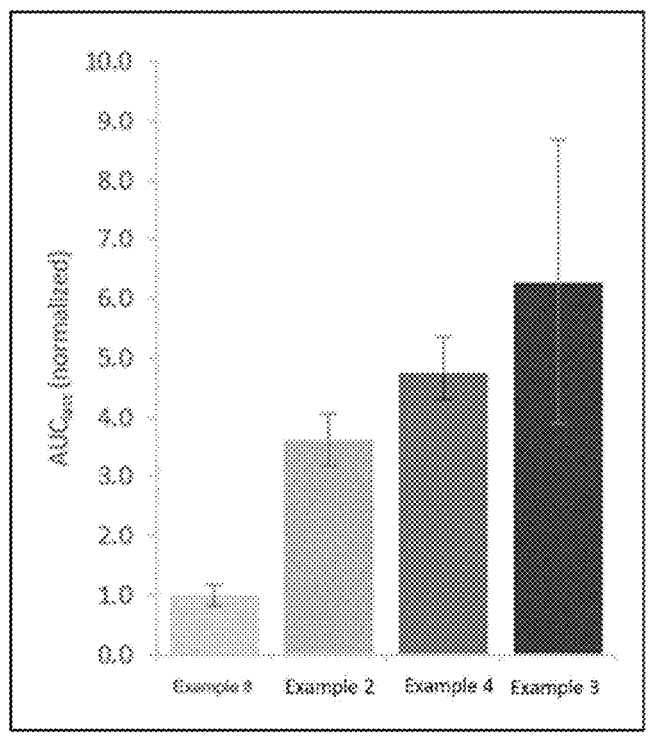
Figure 7:
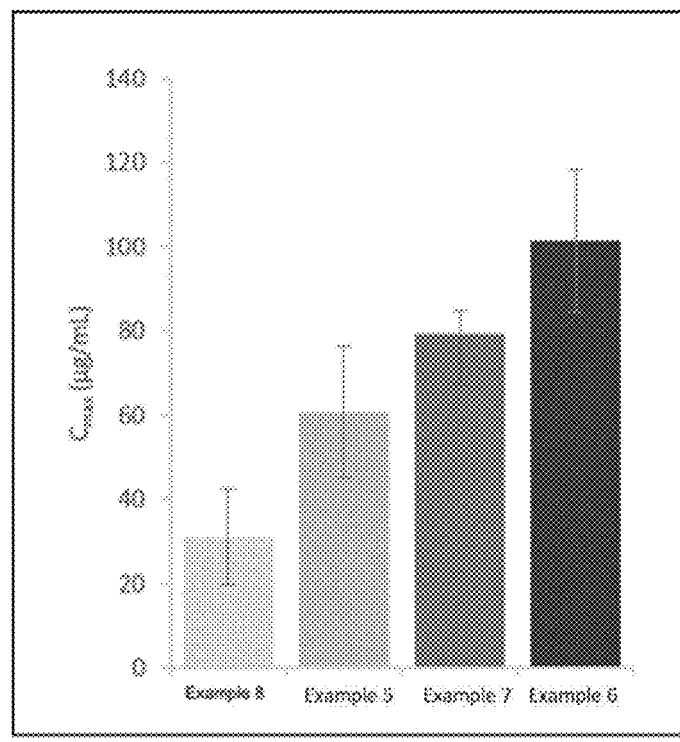
FIGS. 7 and 8 show absolute and relative $C_{max}$ results for formulations of Compound 1 as a suspension and in enteric coated capsules, and Compound 2 and Compound 3 separately in enteric coated capsules.
Figure 8:
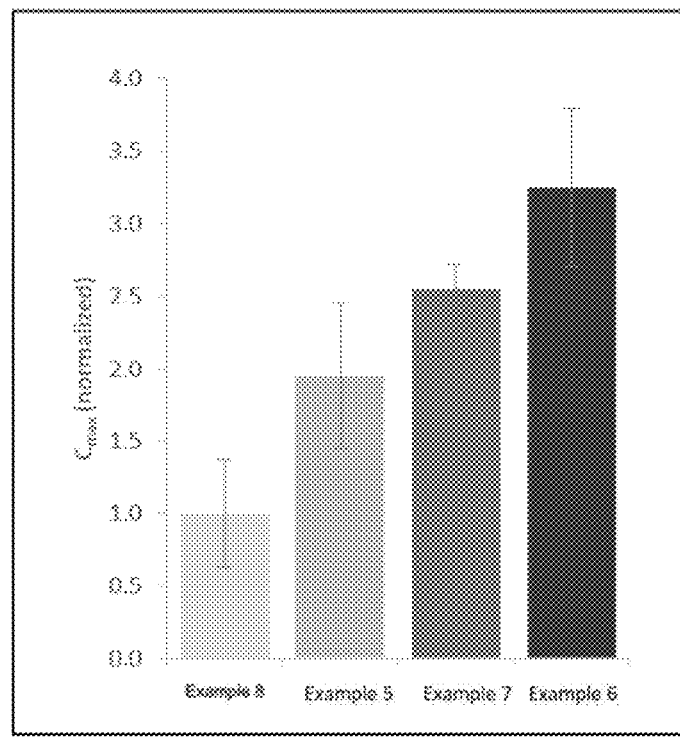
Figure 9:
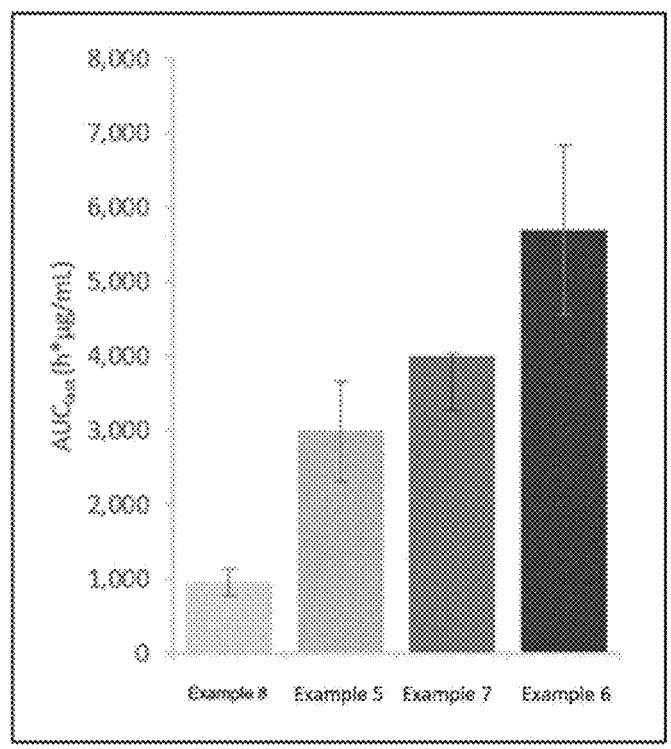
FIGS. 9 and 10 show absolute and relative AUC results for formulations of Compound 1 as a suspension and in enteric coated capsules, and Compound 2 and Compound 3 separately in enteric coated capsules.
Figure 10:
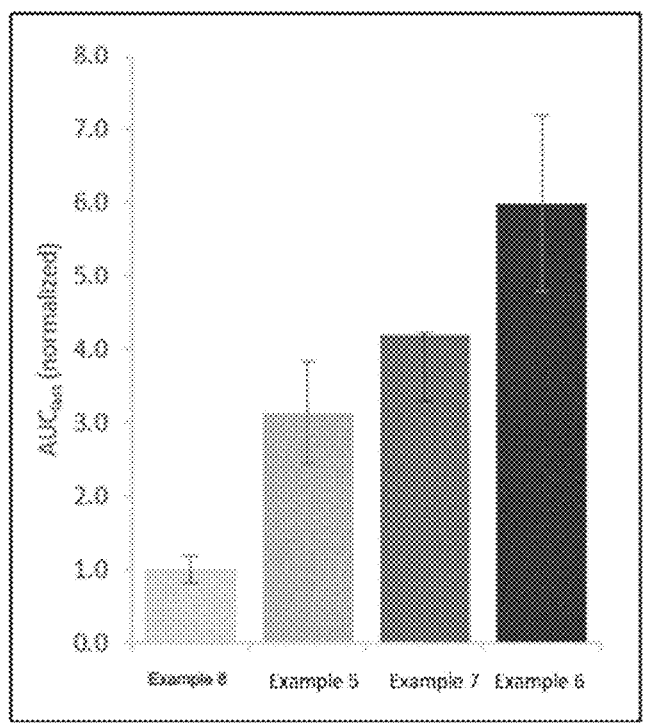

The results for the single dose oral pharmacokinetic study in rabbits are tabulated in Tables 3 to 8 below and are shown graphically in FIGS. 1 to 10.

The results show that there is an increase of between 50 and 100% in the systemic exposure of 4-chloro-N-[2-[(4-chlorophenyl)methyl]-3-oxo-1,2,4-thiadiazol-5-yl]benzamide when it is administered as a dry milled sodium salt (compound 2) compared to free base active ingredient (compound 1)—compare Examples 2 and 3, compare also Example 5 and 6; FIGS. 3 to 10. The dry milled potassium salt (compound 3) gave a more modest improvement compared with the milled free base active ingredient—compare Examples 2 and 4, compare also Examples 5 and 7; FIGS. 3 to 10.

When compared to a standard suspension of the active ingredient (example 8), there was a surprising and substantial (up to six-fold) increase in the systemic exposure of 4-chloro-N-[2-[(4-chlorophenyl)methyl]-3-oxo-1,2,4-thiadiazol-5-yl]benzamide when the active ingredient was administered as a dry milled sodium salt (compound 2) in either non-coated or enteric-coated capsules Thus, the systemic exposure of 4-chloro-N-[2-[(4-chlorophenyl)methyl]-3-oxo-1,2,4-thiadiazol-5-yl]benzamide is increased by administration of the compound in the form of an alkali metal salt. The greatest improvements in systemic exposure were observed when the drug was administered in the form of the sodium salt.

TABLE 3

Mean Plasma Pharmacokinetic Parameters For Compound 1 (4-chloro-N-[2-((4-chlorophenyl)methyl]-3-oxo-1,2,4-thiadiazol-5-yl]benzamide)

| | Example | | |
|---|---|---|---|
| | 2 | 5 | 8 |
| Compound No. | 1 | 1 | 1 |
| Vehicle | Non-coated capsule | Enteric coated capsule | Suspension |
| Dose (mg/kg b.w.) | 90 | 90 | 90 |
| $C_{max}$ (μg/mL) | 63.70 ± 3.79 | 60.8 ± 15.7 | 31.2 ± 11.5 |
| $T_{max}$ (h) | 32.00 ± 13.86 | 40.00 ± 13.86 | 19 ± 9 |
| $AUC_{last}$ (h*μg/mL) | 3448 ± 405.1 | 2988 ± 665.8 | 952 ± 175 |
| $AUC_{inf}$ (h*μg/mL) | 7394 ± 3873 | 18639 ± 12808 | 1123 ± 259.1 |
| $AUC_{extrap}$ (%) | 46.71 ± 19.06 | 82.44 ± 9.84 | 14 ± 9 |
| $T_{1/2}$ (h) | 68.17 ± 43.03 | 252.2 ± 133.0 | 36 ± 8 |
| $MRT_{last}$ (h) | 36.86 ± 2.56 | 45.17 ± 2.54 | 25 ± 5 |

TABLE 4

Plasma Concentration of Compound 1 (4-chloro-N-[2-[(4-chlorophenyl)methyl]-3-oxo-1,2,4-thiadiazol-5-yl]benzamide)

| | Plasma concentration of dry milled compound 1 (ng/mL) | | | | | |
|---|---|---|---|---|---|---|
| | Example 2 | | Example 5 | | Example 8 | |
| Time (h) | Mean | SD | Mean | SD | Mean | SD |
| 0.00 | 0.000 | 0.000 | 0.000 | 0.000 | 0 | 0 |
| 0.16 | 0.000 | 0.000 | 0.000 | 0.000 | 1211 | 502 |
| 0.25 | 0.000 | 0.000 | 0.000 | 0.000 | 4421 | 3757 |
| 0.50 | 50.474 | 87.424 | 0.000 | 0.000 | 7250 | 3732 |
| 1.00 | 386.171 | 538.817 | 0.000 | 0.000 | 9387 | 4013 |
| 2.00 | 1530.898 | 1490.214 | 5.857 | 10.144 | 10099 | 4801 |
| 4.00 | 13407.634 | 5140.695 | 206.003 | 224.379 | 11642 | 3964 |
| 6.00 | 25336.370 | 5542.720 | 307.917 | 452.404 | 138880 | 3937 |
| 8.00 | 39160.355 | 4845.192 | 1505.092 | 1239.461 | 28718 | 13800 |
| 24.00 | 63648.538 | 3803.119 | 45705.076 | 7965.993 | 18423 | 10570 |
| 48.00 | 54789.036 | 11519.885 | 59671.800 | 16461.504 | 8831 | 5336 |
| 72.00 | 35657.688 | 11014.522 | 52298.238 | 22101.996 | 3032 | 1914 |
| Lower limit of quantification | | | 11.062 ng/mL | | | |

TABLE 5

Mean Plasma Pharmacokinetic Parameters For Dry Milled Compound 2 (4-chloro-N-[2-[(4-chlorophenyl)methyl]-3-oxo-1,2,4-thiadiazol-5-yl]benzamide sodium salt)

| | Example | |
|---|---|---|
| | 3 | 6 |
| Compound No. | 2 | 2 |
| Vehicle | Non-coated capsule | Enteric- coated capsule |
| Dose (mg/kg b.w.) | 90 | 90 |
| $C_{max}$ (μg/mL) | 98.97 ± 34.56 | 101.4 ± 17.04 |
| $T_{max}$ (h) | 32.00 ± 13.86 | 32.00 ± 13.86 |
| $AUC_{last}$ (h*μg/mL) | 5985 ± 2274 | 5708 ± 1142 |
| $AUC_{inf}$ (h*μg/mL) | 38101 ± 34673 | 55694 ± 22737 |
| $AUC_{extrap}$ (%) | 79.01 ± 8.87 | 88.81 ± 3.497 |
| $T_{1/2}$ (h) | 226.7 ± 139.9 | 367.6 ± 109.2 |
| $MRT_{last}$ (h) | 38.79 ± 1.20 | 42.99 ± 1.59 |

TABLE 6

Plasma Concentration of Dry Milled Compound 2 (4-chloro-N-[2-[(4-chlorophenyl)methyl]-3-oxo-1,2,4-thiadiazol-5-yl]benzamide sodium salt)

Plasma concentration of dry milled compound 2 (ng/mL)

| Time (h) | Example 3 Mean | Example 3 SD | Example 6 Mean | Example 6 SD |
|---|---|---|---|---|
| 0.00 | 0.000 | 0.000 | 0.000 | 0.000 |
| 0.16 | 0.000 | 0.000 | 0.000 | 0.000 |
| 0.25 | 51.798 | 64.697 | 0.000 | 0.000 |
| 0.50 | 206.386 | 140.625 | 0.000 | 0.000 |
| 1.00 | 594.725 | 272.012 | 9.027 | 15.636 |
| 2.00 | 1377.183 | 827.033 | 13.276 | 22.995 |
| 4.00 | 15776.855 | 19265.479 | 624.216 | 737.401 |
| 6.00 | 46144.063 | 18439.160 | 11866.638 | 20124.750 |
| 8.00 | 71215.612 | 27009.076 | 18413.782 | 30416.066 |
| 24.00 | 98809.233 | 34294.286 | 99879.409 | 15454.358 |
| 48.00 | 93029.388 | 38125.274 | 101178.612 | 17297.678 |
| 72.00 | 84071.553 | 36175.531 | 90966.319 | 16842.785 |
| Lower limit of quantification | 11.062 ng/mL | | | |

TABLE 7

Mean Plasma Pharmacokinetic Parameters For Dry Milled Compound 3 (4-chloro-N-[2-[(4-chlorophenyl)methyl]-3-oxo-1,2,4-thiadiazol-5-yl]benzamide potassium salt)

| | Example 4 | Example 7 |
|---|---|---|
| Compound No. | 3 | 3 |
| Vehicle | Non-coated capsule | Enteric-coated capsule |
| Dose (mg/kg b.w.) | 90 | 90 |
| $C_{max}$ (µg/mL) | 81.90 ± 10.4 | 79.47 ± 5.43 |
| $T_{max}$ (h) | 40.00 ± 13.86 | 48.00 ± 0.00 |
| $AUC_{last}$ (h*µg/mL) | 4526 ± 589.4 | 3993 ± 43.27 |
| $AUC_{inf}$ (h*µg/mL) | 9370 ± 3377 | 18614 ± 13840 |
| $AUC_{extrap}$ (%) | 52.23 ± 10.63 | 69.48 ± 19.80 |
| $T_{1/2}$ (h) | 71.56 ± 22.63 | 188.57 ± 158.39 |
| $MRT_{last}$ (h) | 39.563 ± 3.879 | 41.971 ± 0.696 |

TABLE 8

Plasma Concentration of Dry Milled Compound 3 (4-chloro-N-[2-[(4-chlorophenyl)methyl]-3-oxo-1,2,4-thiadiazol-5-yl]benzamide potassium salt)

Plasma concentration of dry milled compound 3 (ng/mL)

| Time (h) | Example 4 Mean | Example 4 SD | Example 7 Mean | Example 7 SD |
|---|---|---|---|---|
| 0.00 | 0.000 | 0.000 | 0.000 | 0.000 |
| 0.16 | 169.000 | 264.220 | 0.000 | 0.000 |
| 0.25 | 255.336 | 379.795 | 0.000 | 0.000 |
| 0.50 | 457.796 | 516.389 | 0.000 | 0.000 |
| 1.00 | 2349.624 | 3185.747 | 4.721 | 8.177 |
| 2.00 | 4456.537 | 3014.162 | 93.881 | 84.157 |
| 4.00 | 16997.495 | 5642.942 | 2558.779 | 3400.345 |
| 6.00 | 21418.736 | 5907.019 | 7906.592 | 8461.297 |
| 8.00 | 39754.464 | 15506.499 | 16147.149 | 13934.820 |
| 24.00 | 75168.570 | 5463.233 | 66084.614 | 5140.470 |
| 48.00 | 77379.051 | 17862.078 | 79465.599 | 5432.733 |
| 72.00 | 60164.693 | 23815.560 | 49785.289 | 7425.826 |
| Lower limit of quantification | 11.062 ng/mL | | | |

Examples 9 and 10

The following studies (referred to as Examples 9 and 10) provided comparative single dose oral pharmacokinetics data for Compound 2 (the sodium salt of Compound 1) using enteric-coated capsules in male New Zealand White Rabbits in the presence of a pH modifier (magnesium oxide). The studies were conducted using the methods described above in respect of Examples 2 to 8, except where indicated below.

Enteric coated gelatin capsules were individually filled with the following:

Ex. 9: Compound 2 (62.5 mg), sodium docusate (6.25 mg), PVP K30 (0.625 mg) and magnesium oxide (125 mg).

Ex. 10: Compound 2 (62.5 mg), sodium docusate (6.25 mg), PVP K30 (0.625 mg) and mannitol (125 mg).

Animals received 25 mg/kg b.w. of Compound 2 in a single dose.

Results

The results for the single dose oral pharmacokinetic study in rabbits are tabulated in Table 9 below.

The results show that there is an increase in the systemic exposure of 4-chloro-N-[2-[(4-chlorophenyl)methyl]-3-oxo-1,2,4-thiadiazol-5-yl]benzamide when Compound 2 is formulated together with an alkaline excipient in comparison with formulation in the absence of an alkaline excipient.

TABLE 9

Mean Plasma Pharmacokinetic Parameters For Compound 2 co-formulated with an alkaline excipient

| | Example 9 | Example 10 |
|---|---|---|
| Compound No. | 2 | 2 |
| Vehicle | Enteric coated capsule with MgO | Enteric coated capsule with mannitol |
| Dose (mg/kg b.w.) | 25 | 25 |
| $C_{max}$ (µg/mL) | 49.60 ± 4.80 | 47.43 ± 7.06 |
| $T_{max}$ (h) | 24.00 ± 0.00 | 32.00 ± 13.86 |
| $AUC_{last}$ (h*µg/mL) | 1703.93 ± 247.60 | 1472.50 ± 78.72 |
| $MRT_{last}$ (h) | 27.67 ± 0.11 | 29.98 ± 1.73 |

Example 11

The following study is a single dose oral pharmacokinetics study for Compound 2 using enteric-coated capsules in male New Zealand White Rabbits in the presence of a pH modifier (magnesium oxide). The study was conducted using the methods described above in respect of Examples 2 to 8, except where indicated below.

Enteric coated gelatin capsules were individually filled with Compound 2 (106 mg, as obtained in Example 1f), sodium docusate (10.6 mg), PVP K30 (1.1 mg) and magnesium oxide (100 mg).

Animals received 53 mg/kg b.w. of Compound 2 (equivalent to 50 mg/kg Compound 1) in a single dose.

Results

The results for the single dose oral pharmacokinetic study in rabbits are tabulated in Table 10 below.

The results show that there is a significant amount of systemic exposure of 4-chloro-N-[2-[(4-chlorophenyl)methyl]-3-oxo-1,2,4-thiadiazol-5-yl]benzamide when Compound 2 is formulated together with an alkaline excipient.

TABLE 10

Mean Plasma Pharmacokinetic Parameters For Compound 2 co-formulated with an alkaline excipient

|  | Example 11 |
| --- | --- |
| Compound No. | 2 |
| Vehicle | Enteric coated capsule with MgO |
| Dose (mg/kg b.w.) | 53 mg/kg b.w. (equivalent to 50 mg/kg b.w of Compound 1) |
| $C_{max}$ (µg/mL) | 153.00 ± 24.33 |
| $T_{max}$ (h) | 48.00 ± 24.00 |
| $AUC_{last}$ (h*µg/ml) | 8925.87 ± 1186.00 |
| $MRT_{last}$ (h) | 40.93 ± 1.43 |

Example 12

The following illustrates representative pharmaceutical tablet dosage forms containing Compound 2 for therapeutic or prophylactic use in humans:

| Ingredient | Quantity (mg) | Quantity (%) |
| --- | --- | --- |
| Compound 2 | 106.06 | 30.30 |
| Microcrystalline cellulose | 66.15 | 18.9 |
| Lactose monohydrate | 132.29 | 37.8 |
| Sodium starch glycollate | 26.25 | 7.5 |
| Colloidal silicon dioxide | 8.75 | 2.5 |
| Magnesium stearate | 10.50 | 3 |
| Total | 350 | 100 |

| Ingredient | Quantity (mg) | Quantity (%) |
| --- | --- | --- |
| Compound 2 | 106.06 | 30.30 |
| Microcrystalline cellulose | 63.81 | 18.23 |
| Lactose monohydrate | 127.63 | 36.47 |
| Sodium starch glycollate | 26.25 | 7.5 |
| Colloidal silicon dioxide | 8.75 | 2.5 |
| Sodium stearyl fumarate | 17.50 | 5 |
| Total | 350 | 100 |

These formulations may be obtained by conventional procedures well known in the pharmaceutical art. The tablets may also be enteric coated by conventional means, for example to provide a coating of polymethacrylate.

The invention claimed is:

1. An alkali metal salt of 4-chloro-N-[2-[(4-chlorophenyl)methyl]-3-oxo-1,2,4-thiadiazol-5-yl]benzamide.

2. The alkali metal salt of claim 1 wherein the alkali metal is sodium.

3. The alkali metal salt of claim 1 wherein the alkali metal salt is potassium.

4. A pharmaceutical formulation comprising the alkali metal salt of claim 1.

5. The pharmaceutical formulation according to claim 4, wherein said alkali metal salt has been milled.

6. The pharmaceutical formulation according to claim 4, wherein the formulation comprises particles containing the alkali metal salt, said particles having a particle size distribution defined by a D90 of less than 10 µm.

7. The pharmaceutical formulation according to claim 6, wherein the particles have a particle size distribution defined by a D90 of less than 9 µm; a D50 of less than 6 µm; a D50 of less than 5 µm; a D10 of less than 2 µm; or a D10 of less than 1.5 µm.

8. The pharmaceutical formulation according to claim 4, wherein the formulation further comprises an enteric coating.

9. The pharmaceutical formulation according to claim 8, wherein the enteric coating comprises beeswax, shellac, ethylcellulose polymers, carboxymethylethylcellulose, hydroxypropyl methylcellulose phthalate, acrylic acid and methacrylic acid copolymers, methacrylic acid copolymers, methyl methacrylate copolymers, ethoxyethyl methacrylates, cyanoethyl methacrylate, methyl methacrylate, copolymers, methacrylic acid copolymers, methyl methacrylate copolymers, methyl methacrylate copolymers, methacrylate copolymers, methacrylic acid copolymer, aminoalkyl methacrylate copolymer, methacrylic acid copolymers, methyl methacrylate copolymers, poly(acrylic acid), poly(methacrylic acid, methacrylic acid alkylamide copolymer, poly(methyl methacrylate), poly(methacrylic acid) (anhydride), methyl methacrylate, polymethacrylate, methyl methacrylate copolymer, poly(methyl methacrylate), poly(methyl methacrylate) copolymer, polyacrylamide, aminoalkyl methacrylate copolymer, poly(methacrylic acid anhydride), glycidyl methacrylate copolymers), cellulose acetate phthalate, or polyvinyl acetate phthalate.

10. The pharmaceutical formulation according to claim 4, wherein the formulation further comprises at least one pharmaceutically acceptable excipient.

11. The pharmaceutical formulation according to claim 4, wherein the formulation further comprises a lubricant, a binder, a filler, a surfactant, a diluent, an anti-adherent, a coating, a flavouring, a colourant, a glidant, a preservative, a sweetener, a disintegrant, an adsorbent, a buffering agent, an antioxidant, a chelating agent, a dissolution enhancer, a dissolution retardant, or a wetting agent, or any combination thereof.

12. The pharmaceutical formulation according to claim 4, wherein the formulation further comprises PVP K30, Na-docusate and mannitol.

13. The pharmaceutical formulation according to claim 4, wherein the formulation is provided in the form of a capsule or a tablet.

14. The pharmaceutical formulation according to claim 13, wherein an enteric coating is present on said capsule or tablet.

15. The pharmaceutical formulation according to claim 13, wherein the capsule or tablet contains particles comprising the alkali metal salt, and wherein each particle is coated with an enteric coating.

16. A pharmaceutical formulation according to claim 4, wherein the alkali metal salt has been milled so that particles containing the alkali metal salt have a particle size distribution defined by a D90 of less than 10 µm, and wherein the formulation further comprises an enteric coating.

17. A method of treatment of a disorder or condition ameliorated by the activation of AMPK comprising administering to a subject in need thereof the alkali metal salt of claim 1.

18. The method of treatment according to claim 17, where in the disorder or condition ameliorated by the activation of AMPK is type 2 diabetes.

19. The method of treatment according to claim 17, where in the disorder or condition ameliorated by the activation of AMPK is a condition associated with hyperinsulinemia selected from the group consisting of obesity and cardiovascular disease.

20. The method of treatment according to claim 17, wherein the disorder or condition ameliorated by the activation of AMPK is cancer.

21. A process for preparing a pharmaceutical formulation of claim 6, wherein the process comprises milling the alkali metal salt to produce the particles having a particle size distribution defined by a D90 of less than 10 μm.

22. The process according to claim 21, wherein the process comprises dry milling.

23. The process according to claim 21, wherein the alkali metal salt is mixed with one or more pharmaceutically acceptable excipients after milling of the alkali metal salt.

24. The process according to claim 21, wherein the pharmaceutical formulation is provided in the form of a capsule or tablet and the process further comprises the step of coating said capsule or tablet with an enteric coating after the milled alkali metal salt is incorporated into said capsule or tablet.

25. The process according to claim 21, wherein the pharmaceutical formulation is provided in the form of a capsule or tablet and the process further comprises the step of applying an enteric coating to the milled alkali metal salt prior to incorporating said milled alkali metal salt into the capsule or tablet.

26. A pharmaceutical formulation comprising the alkali metal salt of claim 2; and at least one pharmaceutically acceptable excipient.

27. A pharmaceutical formulation comprising the alkali metal salt of claim 3; and at least one pharmaceutically acceptable excipient.

28. The pharmaceutical formulation according to claim 26, wherein said alkali metal salt has been milled.

29. The pharmaceutical formulation according to claim 26, wherein the formulation comprises particles containing the alkali metal salt, said particles having a particle size distribution defined by a D90 of less than 10 μm.

30. The pharmaceutical formulation according to claim 29, wherein the particles have a particle size distribution defined by a D90 of less than 9μm; a D50 of less than 6 μm; a D50 of less than 5 μm; a D10 of less than 2 μm; or a D10 of less than 1.5 μm.

31. The pharmaceutical formulation according to claim 26, wherein the formulation further comprises an enteric coating.

32. The pharmaceutical formulation according to claim 31, wherein the enteric coating comprises beeswax, shellac, ethylcellulose polymers, carboxymethylethylcellulose, hydroxypropyl methylcellulose phthalate, acrylic acid and methacrylic acid copolymers, methacrylic acid copolymers, methyl methacrylate copolymers, ethoxyethyl methacrylates, cyanoethyl methacrylate, methyl methacrylate, copolymers, methacrylic acid copolymers, methyl methacrylate copolymers, methyl methacrylate copolymers, methacrylate copolymers, methacrylic acid copolymer, aminoalkyl methacrylate copolymer, methacrylic acid copolymers, methyl methacrylate copolymers, poly(acrylic acid), poly(methacrylic acid, methacrylic acid alkylamide copolymer, poly(methyl methacrylate), poly(methacrylic acid) (anhydride), methyl methacrylate, polymethacrylate, methyl methacrylate copolymer, poly(methyl methacrylate), poly(methyl methacrylate) copolymer, polyacrylamide, aminoalkyl methacrylate copolymer, poly(methacrylic acid anhydride), glycidyl methacrylate copolymers), cellulose acetate phthalate, or polyvinyl acetate phthalate.

33. The pharmaceutical formulation according to claim 26, wherein the formulation further comprises a lubricant, a binder, a filler, a surfactant, a diluent, an anti-adherent, a coating, a flavouring, a colourant, a glidant, a preservative, a sweetener, a disintegrant, an adsorbent, a buffering agent, an antioxidant, a chelating agent, a dissolution enhancer, a dissolution retardant, or a wetting agent, or any combination thereof.

34. The pharmaceutical formulation according to claim 26, wherein the formulation further comprises PVP K30, Na-docusate and mannitol.

35. The pharmaceutical formulation according to claim 26, wherein the formulation is provided in the form of a capsule or a tablet.

36. The pharmaceutical formulation according to claim 35, wherein an enteric coating is present on said capsule or tablet.

37. The pharmaceutical formulation according to claim 35, wherein the capsule or tablet contains particles comprising the alkali metal salt, and wherein each particle is coated with an enteric coating.

38. A pharmaceutical formulation according to claim 26, wherein the alkali metal salt has been milled so that particles containing the alkali metal salt have a particle size distribution defined by a D90 of less than 10 μm, and wherein the formulation further comprises an enteric coating.

39. A method of treatment of a disorder or condition ameliorated by the activation of AMPK comprising administering to a subject in need thereof the alkali metal salt of claim 2.

40. The method of treatment according to claim 39, wherein the disorder or condition ameliorated by the activation of AMPK is type 2 diabetes.

41. The method of treatment according to claim 39, wherein the disorder or condition ameliorated by the activation of AMPK is a condition associated with hyperinsulinemia selected from the group consisting of obesity and cardiovascular disease.

42. The method of treatment according to claim 39, wherein the disorder or condition ameliorated by the activation of AMPK is cancer.

43. A process for preparing a pharmaceutical formulation of claim 29, wherein the process comprises milling the alkali metal salt to produce the particles having a particle size distribution defined by a D90 of less than 10 μm.

44. The process according to claim 43, wherein the process comprises dry milling.

45. The process according to claim 43, wherein the alkali metal salt is mixed with one or more pharmaceutically acceptable excipients after milling of the alkali metal salt.

46. The process according to claim 43, wherein the pharmaceutical formulation is provided in the form of a capsule or tablet and the process further comprises the step of coating said capsule or tablet with an enteric coating after the milled alkali metal salt is incorporated into said capsule or tablet.

47. The process according to claim 43, wherein the pharmaceutical formulation is provided in the form of a capsule or tablet and the process further comprises the step of applying an enteric coating to the milled alkali metal salt prior to incorporating said milled alkali metal salt into the capsule or tablet.

* * * * *